US011564790B2

(12) United States Patent
Aguilar

(10) Patent No.: US 11,564,790 B2
(45) Date of Patent: *Jan. 31, 2023

(54) SKIN PRINTER

(71) Applicant: Mariela Aguilar, San Jose, CA (US)

(72) Inventor: Mariela Aguilar, San Jose, CA (US)

(73) Assignee: Bao Tran, Saratoga, CA (US)

( * ) Notice: Subject to any disclaimer, the term of this patent is extended or adjusted under 35 U.S.C. 154(b) by 669 days.

This patent is subject to a terminal disclaimer.

(21) Appl. No.: 16/601,503

(22) Filed: Oct. 14, 2019

(65) Prior Publication Data

US 2020/0054440 A1    Feb. 20, 2020

Related U.S. Application Data

(63) Continuation of application No. 15/947,791, filed on Apr. 7, 2018, now Pat. No. 10,507,098, which is a continuation of application No. 14/746,631, filed on Jun. 22, 2015, now Pat. No. 9,968,437.

(51) Int. Cl.
| | |
|---|---|
| *A61L 27/00* | (2006.01) |
| *A61L 27/38* | (2006.01) |
| *A61F 2/10* | (2006.01) |
| *A61L 27/60* | (2006.01) |
| *A61L 27/24* | (2006.01) |
| *A61L 27/48* | (2006.01) |
| *A61L 27/54* | (2006.01) |
| *B33Y 10/00* | (2015.01) |
| *A61F 2/28* | (2006.01) |
| *A61F 2/30* | (2006.01) |
| *B33Y 80/00* | (2015.01) |
| *G06T 7/73* | (2017.01) |

(52) U.S. Cl.
CPC .............. *A61F 2/105* (2013.01); *A61L 27/24* (2013.01); *A61L 27/38* (2013.01); *A61L 27/3834* (2013.01); *A61L 27/48* (2013.01); *A61L 27/54* (2013.01); *A61L 27/60* (2013.01); *B33Y 10/00* (2014.12); *A61F 2/28* (2013.01); *A61F 2002/30985* (2013.01); *A61F 2210/0004* (2013.01); *A61F 2240/002* (2013.01); *A61F 2240/004* (2013.01); *A61L 2300/414* (2013.01); *B33Y 80/00* (2014.12); *G06T 7/74* (2017.01)

(58) Field of Classification Search
None
See application file for complete search history.

(56) References Cited

U.S. PATENT DOCUMENTS

| | | | |
|---|---|---|---|
| 9,968,437 B2* | 5/2018 | Tran | B33Y 10/00 |
| 10,507,098 B2* | 12/2019 | Aguilar | A61L 27/38 |
| 2003/0175410 A1* | 9/2003 | Campbell | A61L 27/38 |
| | | | 623/23.72 |

(Continued)

OTHER PUBLICATIONS

Biofabris [online] retrieved on Aug. 4, 2022 from: http://biofabris.com.br/en/wake-forest-3d-prints-skin-cells-onto-burn-wounds/#:~:text=Scientists%20have%20developed%20a%20method,somewhere%20on%20the%20patient%27s%20body; Mar. 11, 2014: 2 pages.) (Year: 2014).*

(Continued)

*Primary Examiner* — Ernst V Arnold
(74) *Attorney, Agent, or Firm* — PatentPC; Bao Tran

(57) ABSTRACT

A method includes forming a scaffold and seeding the scaffold with live cells; growing the cells in the scaffold; and 3D printing the cells into a living subject, where the cells continue to live in the living subject.

19 Claims, 4 Drawing Sheets

(56) References Cited

U.S. PATENT DOCUMENTS

2014/0012225 A1* 1/2014 Yoo .................. A61L 27/225
                                                                             604/503

OTHER PUBLICATIONS

Alyn Griffiths (3D-printing BioPen "draws" with living cells to repair damaged bones; [online] retrieved on Aug. 4, 2022 from: https://www.dezeen.com/2013/12/23/3d-printing-biopen-draws-bone-repairs-with-stem-cells/; Dec. 23, 2013; 5 pages). (Year: 2013).*

* cited by examiner

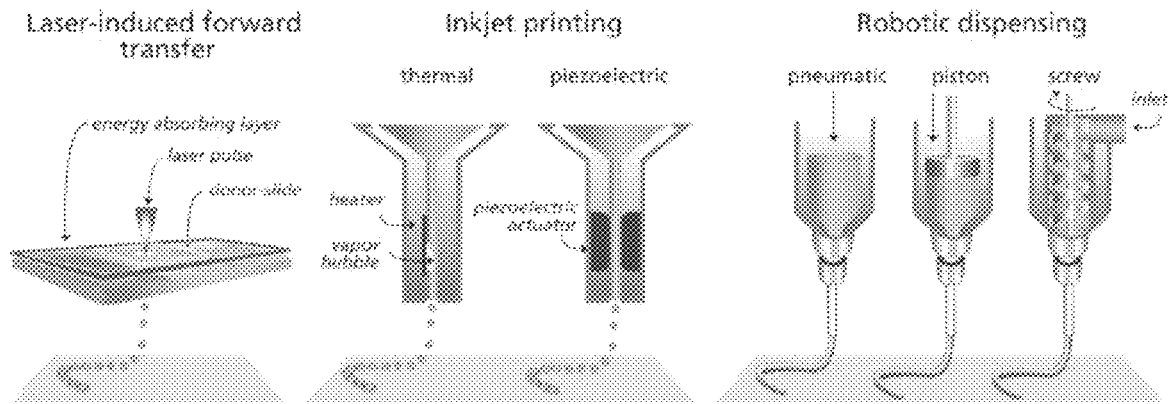

FIG. 3

| |
|---|
| Preparing 300 a wound region (e.g., NPWT—debridement/irrigation, dressings to manage exudate, reduce/eliminate infection, create vascularized granular bed of tissue). |
| Imaging 302 the wound using the pen imaging system and model a graft in 3D from the wound image. |
| Obtaining 304 dermal cells from donor site (estimating a ratio, such as estimating a 1:5 ratio). |
| Preparing 306 a live cell suspension using the dermal cells from the donor site and insert the cartridge with the live cell suspension into the pen. |
| 3D printing 308 onto the wound region an acellular dermal matrix (ADM) scaffold with collagen and hyaluronic acid seeded with live cells processed from the autologous graft. |
| Printing the ADM scaffold 310, securing with sutures and covering with a suitable bandage. |
| Optionally an electrical field is applied to the wound region during printing. Other options include pressure-relieving devices, hyperbaric or topically applied oxygen, whirlpool/pulsed lavage, negative pressure therapy, ultrasound, topical antibiotics, and cytokine growth factors. Electrical stimulation (ES) can provide therapeutic levels of electrical current may be delivered into the wound tissue from an external source. |

| |
|---|
| Place Deionized Water in the vessel where batch has to be manufactured |
| Add item Carbomer, Allantoin, Dipotassium Glycerrhizate, and Disodium EDTA mixing and mix for 10-20 minutes |
| Add all remaining items in Table 1 except for Triethanolamine to the batch one by one |
| Mix the batch for 5-10 minutes and add Triethanolamine with mixing |
| Mix the batch for 5-10 minutes and take collagen sample for QC |
| Phosphorylate the collagen and 3D print the collagen onto the damaged skin |

SKIN PRINTER

BACKGROUND

The present invention relates to 3D bioprinting.

SUMMARY

A method of healing a skin wound includes
  imaging the skin wound using an imager including a supply cartridge;
  obtaining dermal cells from a donor site; preparing a live cell suspension using the dermal cells from the donor site and insert the supply cartridge with the live cell suspension into the pen;
  3D printing onto the wound region an acellular dermal matrix (ADM) scaffold with collagen and seeded with live cells processed from the autologous graft; and
  securing with sutures and covering with a suitable bandage.

In another aspect, a process for printing an object includes:
  providing a 3D printing engine in a pen body with a camera;
  imaging a target area with the camera; and
  injecting materials onto the target area based on the imaged target area.

In another aspect, a process for printing an object includes:
  providing a 3D printing engine in a pen body with a camera;
  imaging a skin area with the camera; and
  injecting materials onto the skin area based on the imaged target area to heal the skin.

In another aspect, a process for printing an object includes:
  providing a 3D printing engine;
  injecting cell with collagen and hyaluronic acid onto the target area based on the imaged target area; and
  photocrosslinking the hyaluronic at each deposition to cure a layer of the object at a time.

In a further aspect, a process for printing a biological object, comprising:
  forming a hyaluronic acid interpenetrating network (HA IPN); and
  3D printing a substrate with the HA IPN.

The HA IPN can be formed using one of: physical or chemical means. The physical means comprise ionic, stereocomplex, or thermal techniques. The chemical cross-linking comprises polymerization using UV irradiation or wet chemical techniques.

In yet another aspect, a method of healing a skin wound, includes
  imaging the skin wound using an imager including a supply cartridge;
  obtaining dermal cells from a donor site;
  preparing a live cell suspension using the dermal cells from the donor site and insert the supply cartridge with the live cell suspension into the pen;
  3D printing onto the wound region an acellular dermal matrix (ADM) scaffold with collagen and seeded with live cells processed from the autologous graft; and
  securing with sutures and covering with a suitable bandage.

Implementations may include auto-grafting a three-dimensional irregularly-shaped skin graft product. The method may include printing a quantity of harvested skin cells. The method may include imaging the wound, wherein the harvested skin cells comprises a quantity of living skin cells from a patient with an imaged wound and a quantity of material not from the patient with the imaged wound.

In yet another aspect, a wound healing composition includes deionized water; carbomer, allantoin, dipotassium glycerrhizate, disodium EDTA (ethylenediaminetetraacetic acid), collagen, tiethanolamine; and PX3 Phosphorus (Othophosphoric Acid) for phosphorylating the collagen.

In another aspect, a process for forming the wound healing solution is also disclosed. Deionized Water is placed in a vessel where batch has to be manufactured. Next, Carbomer, Allantoin, Dipotassium Glycerrhizate, and Disodium EDTA are added and mixed for 10-20 minutes. The remaining items in Table 1, except for Tiethanolamine, are added to the batch one by one. The batch is mixed for 5-10 minutes and Tiethanolamine is added with mixing. The batch is mixed for 5-10 minutes and the resulting collagen sample(s) can be taken for QC.

In another aspect, a process for forming a wound healing composition includes: depositing deionized water in a vessel; adding carbomer, allantoin, dipotassium glycerrhizate, and disodium EDTA (ethylenediaminetetraacetic acid) one at a time into a batch and mixing the batch for a predetermined period; adding collagen and mixing the batch; adding tiethanolamine and mixing the batch; and phosphorylating the collagen with PX3 Phosphorus (Othophosphoric Acid).

In yet another aspect, a method of reproducing a biological object by 3D-imaging the object and generating a mold using a 3D printer; obtaining cells from a donor site on the object; preparing a live cell suspension using the cells from the donor site; forming a scaffold with collagen and hyaluronic acid and seeding the scaffold with live cells; and surgically implanting the object into a living subject, where the cells continue to live in the living subject.

In a further aspect, a system produces functional human tissue as follows:
  particular cell is chosen for particular organ requirements "bio-ink" created from cultured cells, and inserted into a bio-print head component
  HA hydrogels are formed with synthetic or cross-linked materials in the core and surrounded by lightly cross-linked HAs or non-cross-linked HA to reduce risk of tissue rejection
  slow release drug modules containing Ciprofloxacin or suitable antibiotic keeps tissue reaction in control for about six months to minimize tissue rejection and tissue scarring buildup
  cells are then layered among the HA hydrogels until the tissue is produced
  layers in-between HA act as structural support for tissue growth
  "supportive scaffold materials" include HA, fibrin and collagen hydrogels
  hydrogels fill up spaces in-between the layers and as structural support and fuse different cell samples to create larger tissues
  build vascularization with stem of arteries, capillaries, and veins that support the organ to deliver nutrients and remove waste created by the cells.

In one embodiment, the printer creates blood vessels distinct layers or tunics. The tunics surround the central blood-containing space with an innermost tunic (Tunica Intima) with a smooth, friction reducing lining and an outermost layer(Tunica Externa) composed of loosely woven collagen fibers that protect the blood vessel and anchor it to surrounding structures. Optionally, for blood transport, a mid layer (Tunica Media) can be formed with muscle cells that contract and relax, and the elastin allows vessels to stretch and recoil.

In another aspect, a bio-printer prints organs with a hydrogel filler that is cross-linked and then tissues/cells are grown thereon. In one embodiment, the hydrogel can be HA or a slowly degradable synthetic hydrogel filler, consisting of polyvinyl alcohol (8%) gel and water (92%), cross-linked by a physical process of freezing/thawing cycles. The PVA can be dissolved using water over time, as dictated by the cross-linking process.

In another aspect, a bio-printer prints organs with a slowly degradable synthetic hydrogel filler, consisting of polyvinyl alcohol (8%) gel and water (92%), cross-linked by a physical process of freezing/thawing cycles. After cells are grown on the filler, the filler is dissolved in water or blood.

In yet another aspect, the 3D printer can dispense a natural or modified starch, a protein and a cross-linking agent such as an aldehyde, an epoxide or other suitable agent. The reaction of the cross-linking agent with the starch and protein causes the formation of starch-protein linkages, starch-starch linkages, and protein-protein linkages. The compositions of the invention are formed by combining the protein, starch and cross-linking agent in a solution such as aqueous methanol, ethanol, isopropanol, buffer solutions, and the like, and then reducing the water content to a predetermined amount. The present compositions are useful as molding materials for forming articles of various shapes, forms and sizes. It was unexpectedly found that articles formed from the present compositions have an increased level of water-resistance resulting in improved structural stability and resistance to disintegration due to exposure to water, as compared to articles formed from other types of starch-protein compositions. The composition of the invention includes a natural or modified starch that is capable of being cross-linked together by means of a suitable cross-linking agent to form a starch to starch cross-link, and with protein to form a starch to protein cross-link. The composition contains an amount of starch in combination with the protein that is effective to provide a cross-linked starch-protein thermoplastic composition that can be molded into an article that has the desired level of structural stability and water resistance. Native or natural starches that are useful according to the invention include, for example, starch derived from corn, potato, tapioca, rice, wheat, rye, oats, barley, sorghum, mung bean, sweet potato, high am lose corn, waxy corn (maize), waxy rice, and the like. Alternatively, the starch can be presented in the form of a cereal flour, such as milled wheat, oats, corn, rye and the like. Starches, that have been chemically modified, as for example, by acetylation, oxidation, hydroxypropylation, cationization, phosphorylation, cross-linking or other like process, may also be used according to the invention. Examples of chemically-modified starch materials suitable for use in the present composition include, but are not limited to, aluminum starch octenylsuccinate, carboxymethyl starch. hydroxyethyl starch, hydroxypropyl starch, methyl starch, ethyl starch, methyl hydroxyethyl starch, ethylhydroxypropyl starch, starch phosphate, starch acetate, starch propionamide, starch maleate, cationic starch, cross-linked starch, and the like.

In a further aspect, a 3D printer can deposit materials that are (a) 50-95% by weight starch; (b) 5-50% by weight protein; and (c) an amount of cross-linking agent effective to internally and externally link the starch and protein together to form a water-resistant biodegradable composition; the % by weight being based on the total dry weight of the composition; wherein the composition has a water content of about 3-35% by weight based on the total weight of the composition. The starch is a native starch selected from the group consisting of corn starch, potato starch, wheat starch, rice starch, waxy maize starch, waxy rice starch, high amylose corn starch, tapioca starch, oat starch, rye starch, barley starch, sorghum starch, mung bean starch, sweet potato starch, or any combination thereof. The starch is a chemically modified starch selected from the group consisting of aluminum starch octenylsuccinate, carboxymethyl starch, hydroxyethyl starch, hydroxypropyl starch, methyl starch, ethyl starch, methyl hydroxyethyl starch, ethylhydroxy-propyl starch, starch phosphate, starch acetate, starch propionamide, starch maleate, oxidized starch, cationic starch, starch succinate, cross-linked starch, and any combination thereof 4. The composition according to claim 1, wherein the starch is a physically modified starch that is an cold water-soluble starch, or a pregelatinized starch. The protein is a plant-derived protein selected from the group consisting of soybean protein, zein, gluten, hordein, kafirin, avenin, or any combination thereof. The protein is an animal-derived protein selected from the group consisting of collagen, casein, albumin, gelatin, keratin, or any combination thereof. The protein is derived from a microorganism selected from the group consisting of beer yeast, baker's yeast, or any combination thereof. The amount of cross-linking agent is about 0.1-5% by weight. The cross-linking agent is an aldehyde selected from the group consisting of glutaraldehyde, formaldehyde, glyoxal, acetaldehyde, glyceraldehyde, furfuraldehyde, malonic dialdehyde, succinic dialdehyde, adipic dialdehyde, starch dialdehyde, acrolein, or a combination thereof 11. The composition according to claim 9, wherein the cross-linking agent is an epoxide selected from the group consisting of epichlorohydrin, 3-chloro-1,2-epoxypropane, 3-bromo-1,3-epoxypropane, 3-chloro-1,2-epoxybutane, 3-4-dichloro-1,2-epoxybutane, 4-chloro-1,2-epoxypentane, chloroepoxyoctanes, vinyl cyclohexane dioxide, butadiene dioxide, phosphorus oxychloride, or a mixture of adipic anhydride and acetic anhydride. A plasticizer can be used including a polyhydric alcohol selected from the group consisting of glycerol, glycerol monoacetate, diacetate or triacetate, sorbitol, sorbitan, annitol, maltitol, ethylene glycol, propylene glycol, polyvinyl alcohol, sodium cellulose glycolate, cellulose methyl ether, sodium alginate, sodium diethysuccinate, triethyl citrate, polyethylene glycols, polypropylene glycols, polyethylene propylene glycols, and any combination thereof. A coloring agent can be added to match natural body parts such as nails, or skin color, among others.

In another aspect, an artificial organ is made by printing a scaffold of extracellular matrix that retains the shape of the desired organ. Patient cells and stem cells are placed onto the matrix and cultured them for a few days. The extracellular matrix directed the stem cells to their correct function, essentially 'training' them to function appropriately. Finally, the tissues can be transplanted to the patient as artificial organs.

In yet another aspect, an artificial lung is made by printing a lung collagen matrix to form a scaffold of extracellular matrix that retains the hierarchical branching structures of airways and vasculature. Patient lung cells are placed onto the matrix and cultured them for a few days. The natural extracellular matrix directed the cells to their correct locations, essentially 'training' them to function appropriately. Finally, the tissues can be transplanted to the patient as artificial lungs.

In another aspect, a system can produce artificial organs for testing medication's efficacy, biocompatibility and toxicity.

BRIEF DESCRIPTION OF THE DRAWINGS

FIG. 2A illustrates an embodiment of the 3D printer pen, while FIG. 3 shows exemplary 3D biological printing engines in the 3D printer pen.

FIG. 4 shows an exemplary process for 3D printing and repairing burned skin.

FIG. 5 shows an exemplary process of applying collagen to repair tissue.

DESCRIPTION

Figure 1:
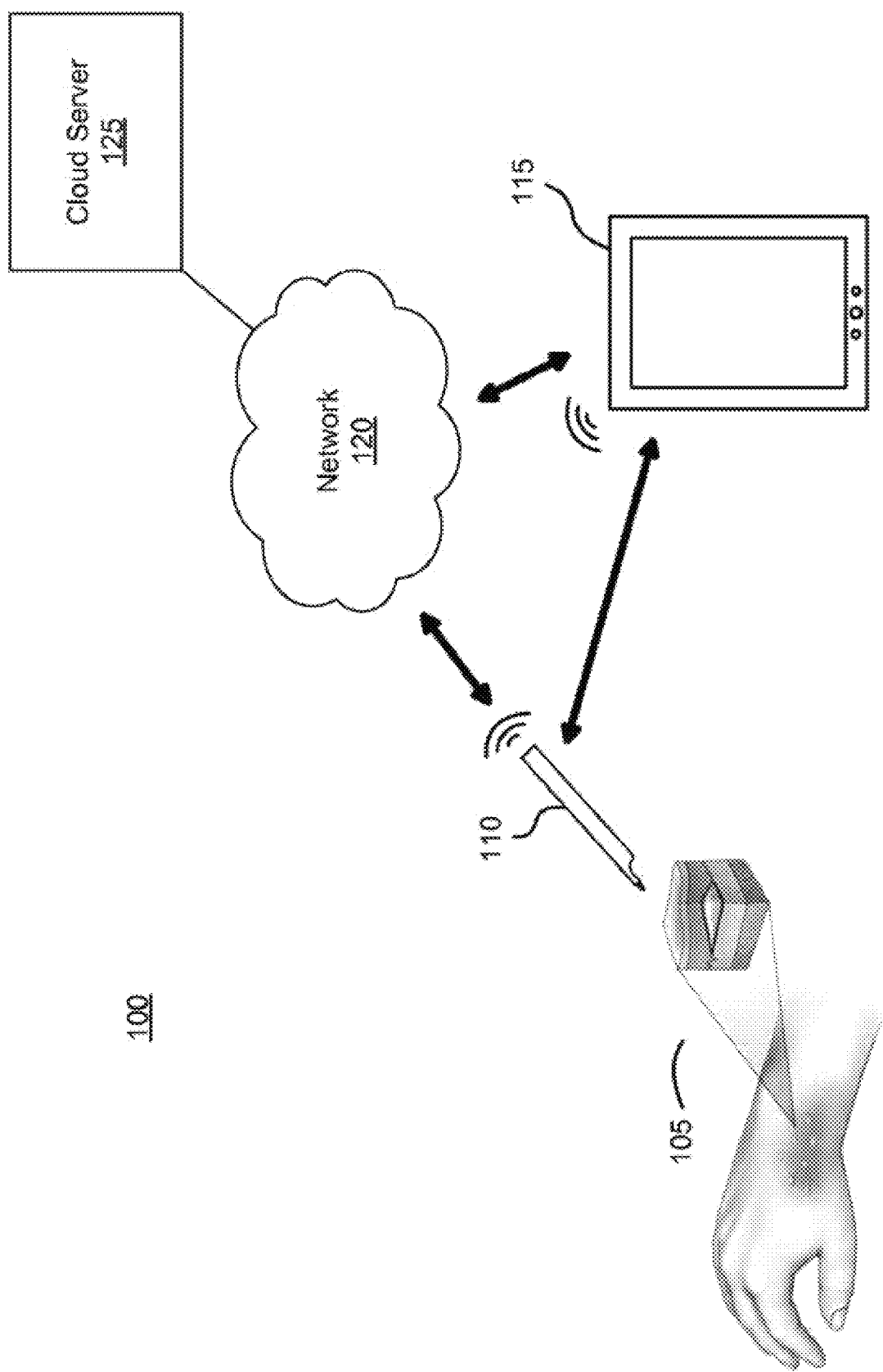
FIG. 1 illustrates an embodiment of a pen-based biological printing system.

FIG. 1 illustrates an embodiment of a pen-based biological printing system 100. The pen-based system comprises a tissue or organ target surface 105, a 3D printer pen 110, a computing device 115, a network 120, and a cloud server 125. In alternative embodiments, different or additional devices may be present such as, for example, additional 3D printer pens 110, biological surfaces 105, and computing devices 115 (or one or more device may be absent). As shown in FIG. 1, the pen system repairs burned skin on a hand. However, other applications are contemplated. In one embodiment, the biological surface 105 can be skin or can be heart, ear, lung, or any suitable organs. Typically, the pen deposits cells in a support scaffold such as hyaluronic acid or collagen, for example. Examples of contents of 3D printer cell dispensed include, autologous fibroblasts, keratinocytes, ECM proteins, growth factors (GF s), cytokines. Examples of contents of 3D printer cell dispensed are, e.g., GF, insulin, PDGF, eNOS. Examples of contents of 3D printer cell dispensed are lyophyllized amniotic membrane. The result is a cultured graft preferably comprising bovine collagen, hyaluronic acid, media, growth factors (GF s), etc.

Although not required, cells can typically be printed in the form of a "cell composition" that contains a liquid carrier for the cells. The cell composition can be in the form of a suspension, solution, or any suitable form. Examples of suitable liquid carriers include, but are not limited to, water, ionic buffer solutions (e.g., phosphate buffer solution, citrate buffer solution, etc.), liquid media (e.g., modified Eagle's medium ("MEM"), Hanks' Balanced Salts, etc.), and so forth. For instance, the use of a liquid carrier in the cell composition can ensure adequate hydration and minimize evaporation of the cells after printing. Various mechanisms may be employed to facilitate the survival of the cells during and/or after printing. Specifically, compounds may be utilized that "support" the printed cells by providing hydration, nutrients, and/or structural support. These compounds may be applied to the substrate using conventional techniques, such as manually, in a wash or bath, through vapor deposition (e.g., physical or chemical-vapor deposition), etc. These compounds may also be combined with the cell composition before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the printer head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc. One example of a collagen gel for facilitating cell growth is described in Collagen As a Substrate for Cell Growth and Differentiation, Methods in Enzymology, Strom and Michalopoulous, Vol. 82. 544-555 (1982) (T. Boland at para 50).

Besides gels, other support compounds may also be utilized in the present invention. Extracellular matrix analogs, for example, may be combined with support gels to optimize or functionalize the gel. One or more growth factors may also be introduced in the printed cell arrays. For example, slow release microspheres that contain one or more growth factors in various concentrations and sequences may be combined with the cell composition to accelerate and direct the cell fusion process. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways may be included in cell aggregates to be printed according to the invention. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following printing of a layer. In addition, adhesives, such as arginine-glycine-aspartic acid ligands, may enhance the adhesion of cells to a gelling polymer or other support compound. In addition, extracellular proteins, extracellular protein analogs, etc., may also be utilized (T. Boland at para 55).

Besides two-dimensional arrays, three-dimensional arrays may also be formed. Three-dimensional cell arrays are commonly used in tissue engineering and biotechnology for in-vitro and in-vivo cell culturing. In general, a three-dimensional array is one which includes two or more layers separately applied to a substrate, with subsequent layers applied to the top surface of previous layers. The layers can, in one embodiment, fuse or otherwise combine following application or, alternatively, remain substantially separate and divided following application to the substrate. Three-dimensional arrays may be formed in a variety of ways in accordance with the present invention. For example, in one embodiment, three-dimensional arrays may be formed by printing multiple layers onto the substrate. (T. Boland at para 60).

The thickness of a printed layer (e.g., cell layer, support layer, etc.) may generally vary depending on the desired application. For example, in some embodiments, the thickness of a layer containing cells is from about 2 micrometers to about 3 millimeters, and in some embodiments, from about 20 micrometers to about 100 micrometers. Further, as indicated above, support compounds, such as gels, are often used to facilitate the survival of printed cells. The present inventors have discovered that the development of a cellular assembly may be increased when the thickness of the support layer(s) (e.g., between cells) is approximately the same as the size of the cells deposited adjacent to the support compound (T. Boland at para 61).

When printing certain types of two-dimensional or three-dimensional arrays, it is sometimes desired that any subsequent cell growth is substantially limited to a predefined region. Thus, to inhibit cell growth outside of this predefined region, compounds may be printed or otherwise applied to the substrate that inhibit cell growth and thus form a boundary for the printed pattern. Some examples of suitable compounds for this purpose include, but are not limited to, agarose, poly(isopropyl N-polyacrylamide) gels, and so forth. In one embodiment, for instance, this "boundary technique" may be employed to form a multi-layered, three-dimensional tube of cells, such as blood vessels. For example, a cell suspension may be mixed with a first gel ("Gel A") in one nozzle, while a second gel ("Gel B") is loaded into another nozzle. Gel A induces cell attachment and growth, while Gel B inhibits cell growth. To form a tube, Gel A and the cell suspension are printed in a circular pattern with a diameter and width corresponding to the diameter and wall thickness of the tube, e.g., from about 3 to about 10 millimeters in diameter and from about 0.5 to about 3 millimeters in wall thickness. The inner and outer patterns are lined by Gel B defining the borders of the cell growth. For example, a syringe containing Gel A and "CHO" cells and a syringe containing Gel B may be connected to the nozzle. Gel B is printed first and allowed to cool for about 1 to 5 minutes. Gel A and CHO cells are then printed on the agarose substrate. This process may be repeated for each layer. (T. Boland at para 62).

The printing of tissues can be done with an appropriate combination of cell and support material, or two or three or more different cell types typically found in a common tissue, preferably along with appropriate support compound or compounds, and optionally but preferably with one or more appropriate growth factors. Cells, support compounds, and growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degredable support material), and some of the ingredients may be printed in the form of a second pattern (e.g., cells in a pattern different from the support, or two different cell types in a different pattern). Again the particular combination and manner of printing will depend upon the particular tissue.

The 3D printer pen 110 is an electronic device that digitally prints tissue or organ surface 105 (e.g., with writing gestures and/or control inputs). The 3D printer pen 110 is communicatively coupled to the computing device 115 either directly or via the network 120. The captured printing gestures and/or control inputs may be transferred from the 3D printer pen 110 to the computing device 115 (e.g., either in real time or at a later time) for use with one or more applications executing on the computing device 115. Furthermore, digital data and/or control inputs may be communicated from the computing device 115 to the 3D printer pen 110 (either in real time or as an offline process) for use with an application executing on the smart pen 110. Commands may similarly be communicated from the 3D printer pen 110 to the computing device 115 for use with an application executing on the computing device 115. The cloud server 125 provides remote storage and/or application services that can be utilized by the 3D printer pen 110 and/or the computing device 115. The pen-based 3D printing system 100 thus enables a wide variety of applications that combine user interactions for tissue/organ printing.

In one embodiment, the 3D printer pen 110 comprises a biofabrication instrument (e.g., an ink-based tissue printing pen, a stylus device without cells, a stylus device that deposits cells, a pencil, or other writing apparatus) with embedded computing components and various input/output functionalities. A user may write with the 3D printer pen 110 on the biological surface 105 as the user would with a conventional pen. During the operation, the 3D printer pen 110 deposits the biological materials and also digitally captures the writing gestures made on the biological surface 105 and stores electronic representations of the writing gestures. The captured writing gestures have both spatial components and a time component. In one embodiment, the 3D printer pen 110 captures position samples (i.e., coordinate information) of the 3D printer pen 110 with respect to the biological surface 105 at various sample times and stores the captured position information together with the timing information of each sample. The captured writing gestures may furthermore include identifying information associated with the particular biological surface 105 such as, for example, identifying information of a tissue (skin/ear/ . . . ) so as to distinguish between data captured with different biological surfaces 105. In another embodiment, the 3D printer pen 110 also captures other attributes of the writing gestures chosen by the user. For example, material to be deposited may be selected by tapping a printed icon on a page or, selecting an icon on a computer display, etc. The biological ink information (material type, line width, line style, etc.) may also be encoded in the captured data.

In an embodiment, the computing device 115 additionally captures contextual data while the 3D printer pen 110 deposits biological materials. In an alternative embodiment, written gestures may instead be captured by biological surface 105 instead of, or in addition to, being captured by the smart pen 110. The contextual data may include audio and/or video from an audio/visual source (e. g., the surrounding room). Contextual data may also include, for example, user interactions with the computing device 115 (e.g. documents, web pages, emails, and other concurrently viewed content), information gathered by the computing device 115 (e.g., geospatial location), and synchronization information (e.g., cue points) associated with time-based content (e.g., audio or video) being viewed or recorded on the computing device 115. The computing device 115 stores the contextual data synchronized in time with the captured writing gestures (i.e., the relative timing information between the captured written gestures and contextual data is preserved). In an alternate embodiment, the 3D printer pen 110 or a combination of a 3D printer pen 110 and a computing device 115 captures contextual data. Furthermore, in an alternate embodiment, some or all of the contextual data can be stored on the 3D printer pen 110 instead of, or in addition to, being stored on the computing device 115.

In one embodiment, the 3D printer pen 110 can automatically recognize/detect biological objects (such as wound outlines) or other pre-existing content on the biological surface 105. In one embodiment, the 3D printer pen 110 directly recognizes the biological object (e.g., by performing image processing and recognition). In another embodiment, the smart pen recognizes positional information of the 3D printer pen 110 and determines what pre-content is being interacted by correlating the captured positional information with known positional information of the pre-existing content. In order to enable communication between the 3D printer pen 110 and the computing device 115, the 3D printer pen 110 and the computing device 115 may establish a "pairing" with each other. The pairing allows the devices to recognize each other and to authorize data transfer between the two devices. Once paired, data and/or control signals may be transmitted between the 3D printer pen 110 and the computing device 115 through wired or wireless means. In one embodiment, both the 3D printer pen 110 and the computing device 115 carry a TCP/IP network stack linked to their respective network adapters. The devices 110, 115 thus support communication using direct (TCP) and broadcast (UDP) sockets with applications executing on each of the 3D printer pen 110 and the computing device 115 able to use these sockets to communicate.

The network 120 enables communication between the smart pen 110, the computing device 115, and the cloud server 125. The network 120 enables the 3D printer pen 110 to, for example, transfer captured contextual data between the smart pen 110, the computing device 115, and/or the cloud server 125, communicate control signals between the smart pen 110, the computing device 115, and/or cloud server 125, and/or communicate various other data signals between the smart pen 110, the computing device 115, and/or cloud server 125 to enable various applications. The network 120 may include wireless communication protocols such as, for example, Bluetooth, WiFi, WiMax, cellular networks, infrared communication, acoustic communication, or custom protocols, and/or may include wired communication protocols such as USB or Ethernet. Alternatively, or in addition, the 3D printer pen 110 and computing device 115 may communicate directly via a wired or wireless connection without requiring the network 120.

The cloud server 125 comprises a remote computing system coupled to the 3D printer pen 110 and/or the computing device 115 via the network 120. For example, in one embodiment, the cloud server 125 provides remote storage for data captured by the 3D printer pen 110 and/or the computing device 115. Furthermore, data stored on the cloud server 125 can be accessed and used by the 3D printer pen 110 and/or the computing device 115 in the context of various applications.

Figure 2A:
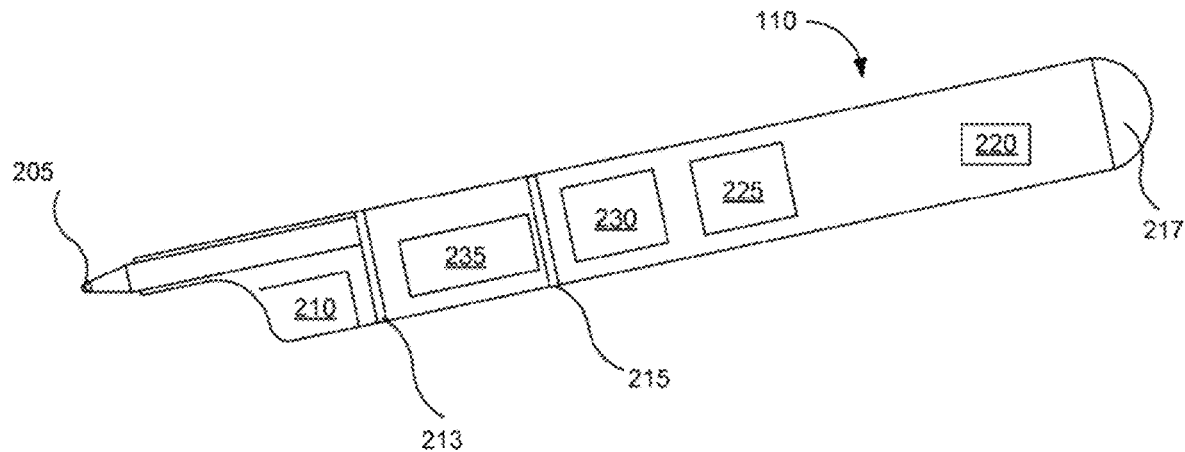

FIG. 2A illustrates an embodiment of the 3D printer pen 110. In the illustrated embodiment, the 3D printer pen 110 comprises a deposit nozzle 205, an imaging system 210, a pen actuation sensor 213, a power state mechanism 215, a tip 217, an I/O port 220, a processor 225, an onboard memory 230, and a battery 235. Other optional components of the 3D printer pen 110 are omitted from FIG. 2A for clarity of description including, for example, status indicator lights, buttons, one or more microphones, a speaker, an audio jack, and a display. In alternative embodiments, the 3D printer pen 110 may have fewer, additional, duplicate, or different components than those illustrated in FIG. 2A.

The deposit nozzle 205 comprises any suitable 3D printing nozzles as shown in FIG. 3, including inkjet, microextrusion, or laser printers. Thermal inkjet printers electrically heat the printhead to produce air-pressure pulses that force droplets from the nozzle, whereas acoustic printers use pulses formed by piezoelectric or ultrasound pressure. Microextrusion printers use pneumatic or mechanical (piston or screw) dispensing systems to extrude continuous beads of material and/or cells. Laser-assisted printers use lasers focused on an absorbing substrate to generate pressures that propel cell-containing materials onto a collector substrate. In one embodiment, 3D printing materials such as hydrogels with suspended cells are generally inserted in disposable plastic syringes in the pen and dispensed, either pneumatic, piston- or screw-driven, in the pen. Rather than single droplets, robotic dispensing yields larger hydrogel strands. In order to maintain the shape of the constructs after printing, hydrogels with higher viscosities are often used. Piston-driven deposition generally provides more direct control over the flow of the hydrogel from the nozzle, due to the delay of the compressed gas volume in the pneumatic systems. Screw-based systems may give more spatial control and are beneficial for the dispensing of hydrogels with higher viscosities.

In one embodiment the deposit nozzle 205 is driven by a syringe-type dispenser. A syringe driver or syringe pump is a small infusion pump (some include infuse and withdraw capability), used to gradually administer small amounts of fluid (with or without medication) to a predetermined region. Syringe pumps use a series of sensors and a motor driven plunger head to infuse liquid at a precise rate. In one embodiment for repairing burns, the target area with the burned skin is secured or fixed to avoid movement. The syringe pump is mounted above the area and deposits tissue and/or continuously administer analgesics (painkillers), antiemetics (medication to suppress nausea and vomiting) and other drugs. This prevents periods during which medication levels in the blood are too high or too low, and avoids the use of multiple tablets (especially in people who have difficulty swallowing). As the medication is administered subcutaneously, the area for administration is practically limitless, although edema may interfere with the action of some drugs.

The deposit nozzle 205 is coupled to a pen down sensor 213, such as a pressure sensitive element. In an alternate embodiment, the deposit nozzle 205 may make electronic marks on a biological surface 105 using a paired projector or electronic display.

The imaging system 210 comprises optics and sensors for imaging an area of a surface near the deposit nozzle 205. The imaging system 210 may be used to automatically detect boundaries of objects for deposition of biological materials thereon. For example, for skin reconstruction, the burned area is captured by the imaging system 210 and when a user scans the burned area, the imaging system 210 would instruct the 3D printer nozzle 205 to deposit materials only over the burned area. In other examples, to reconstruct an ear, the imaging system 210 would deposit the materials only over the appropriate regions to form the ear. In this manner, medical operations can be done in remote regions without hospitals, for example. In addition, the camera can capture handwriting and gestures made with the 3D printer pen 110. In yet other embodiments, the imaging system 210 may include a heat source or light source that heats or illuminates a biological surface 105 in the general vicinity of the deposit nozzle 205. By processing the image of the encoded pattern, the 3D printer pen 110 can determine where the deposit nozzle 205 is in relation to the biological surface 105.

The pen down sensor 213 determines when the smart pen is down. As used herein, the phrase "pen is down" indicates that the deposit nozzle 205 is pressed against or engaged with a biological surface 105. In an embodiment, the pen down sensor 213 produces an output when the pen is down, thereby detecting when the 3D printer pen 110 is being used to write on a surface or is being used to interact with controls or buttons (e.g., tapping) on a control paper. Embodiments of the pen down sensor 213 may include capacitive sensors, piezoresistive sensors, mechanical diaphragms, and electromagnetic diaphragms. The imaging system 210 may further be used in combination with the pen down sensor 213 to determine when the deposit nozzle 205 is touching the biological surface 105. For example, the imaging system 210 could be used to determine if the deposit nozzle 205 is within a particular range of a biological surface 105 using image processing (e.g. based on a fast Fourier transform of a capture image). In an alternate embodiment, a separate range-finding optical, laser, or acoustic device could be used with the pen down sensor 213. In an alternative embodiment, the 3D printer pen 110 can detect vibrations indicating when the pen is writing or interacting with controls on the biological surface 105. In an alternative embodiment, a pen up sensor may be used to determine when the 3D printer pen 110 is up. As used herein, the phrase "pen is up," indicates that the deposit nozzle 205 is neither pressed against nor engaged with a biological surface 105. In some embodiments, the pen down sensor 213 may additionally be coupled with the stylus tip 217, or there may be an additional pen down sensor coupled with or incorporated in the tip 217.

The power status mechanism 215 can toggle the power status of the smart pen 110. The power status mechanism may also sense and output the power status of the smart pen 110. The power status mechanism may be embodied as a rotatable switch integrated with the pen body, a mechanical button, a dial, a touch screen input, a capacitive button, an optical sensor, a temperature sensor, or a vibration sensor. When the power status mechanism 215 is toggled on, the pen's battery 235 is activated, as are the imaging system 210, the input/output device 220, the processor 225, and onboard memory 230. In some embodiments, the power status mechanism 215 toggles status lights, displays, microphones, speakers, and other components of the smart pen 110. In some embodiments, the power status mechanism 215 may be mechanically, electrically, or magnetically coupled to the deposit nozzle 205 such that the deposit nozzle 205 extends when the power status mechanism 215 is toggled on and retracts when the power status mechanism 215 is toggled off. In some embodiments, the power status mechanism 215 is coupled to the deposit nozzle 205 and/or the capacitive tip such that use of the marker and/or capacitive tip 217 toggles the power status. In some embodiments, the power status mechanism 215 may have multiple positions, each position toggling a particular subset of the components in the smart pen 110.

The tip 217 is used to write on or otherwise interact with devices or objects without leaving a physical ink mark. Examples of devices for use with the stylus tip might include tablets, phones, personal digital assistants, interactive whiteboards, or other devices capable of touch-sensitive input. The stylus tip may make use of capacitance or pressure sensing. In some embodiments, the stylus tip may be used in place of or in combination with the deposit nozzle 205.

The input/output (I/O) device 220 allows communication between the 3D printer pen 110 and the network 120 and/or the computing device 115. The I/O device 220 may include a wired and/or a wireless communication interface such as, for example, a Bluetooth, Wi-Fi, WiMax, 3G, 4G, infrared, or ultrasonic interface, as well as any supporting antennas and electronics.

A processor 225, onboard memory 230 (i.e., a non-transitory computer-readable storage medium), and battery 235 (or any other suitable power source) enable computing functionalities to be performed on the smart pen 110. The processor 225 is coupled to the input and output devices (e.g., imaging system 210, pen down sensor 213, power status mechanism 215, stylus tip 217, and input/output device 220) as well as onboard memory 230 and battery 235, thereby enabling applications running on the 3D printer pen 110 to use those components. As a result, executable applications can be stored to a non-transitory computer-readable storage medium of the onboard memory 230 and executed by the processor 225 to carry out the various functions attributed to the 3D printer pen 110 that are described herein. The memory 230 may furthermore store the recorded written and contextual data, either indefinitely or until offloaded from the 3D printer pen 110 to a computing system 115 or cloud server 125.

In an embodiment, the processor 225 and onboard memory 230 include one or more executable applications supporting and enabling a menu structure and navigation through a file system or application menu, allowing launch of an application or of a functionality of an application. For example, navigation between menu items comprises an interaction between the user and the 3D printer pen 110 involving spoken and/or written commands and/or gestures by the user and audio and/or visual feedback from the smart pen computing system. In an embodiment, pen commands can be activated using a "launch line." For example, on dot paper, the user draws a horizontal line from right to left and then back over the first segment, at which time the pen prompts the user for a command. The user then prints (e.g., using block characters) above the line the desired command or menu to be accessed (e.g., Wi-Fi Settings, Playback Recording, etc.). Using integrated character recognition (ICR), the pen can convert the written gestures into text for command or data input. In alternative embodiments, a different type of gesture can be recognized to enable the launch line. Hence, the 3D printer pen 110 may receive input to navigate the menu structure from a variety of modalities.

During a smart pen computing session, the pen-based computing system 100 acquires content that comes in two primary forms, that generated or collected through the operation of the smart pen 110, and that generated in or collected by a computing device 115. This data may include, for example, stroke data, audio data, digital content data, and other contextual data.

As may be further appreciated with reference to FIG. 4, an example of a skin printing process includes:

Preparing 300 a wound region (e.g., NPWT—debridement/irrigation, dressings to manage exudate, reduce/eliminate infection, create vascularized granular bed of tissue).

Imaging 302 the wound using the pen imaging system and model a graft in 3D from the wound image.

Obtaining 304 dermal cells from donor site (estimating a ratio, such as estimating a 1:5 ratio).

Preparing 306 a live cell suspension using the dermal cells from the donor site and insert the cartridge with the live cell suspension into the pne.

3D printing 308 onto the wound region an acellular dermal matrix (ADM) scaffold with collagen and hyaluronic acid seeded with live cells processed from the autologous graft.

Printing the ADM scaffold 310, securing with sutures and covering with a suitable bandage.

Optionally an electrical field is applied to the wound region during printing. Other options include pressure-relieving devices, hyperbaric or topically applied oxygen, whirlpool/pulsed lavage, negative pressure therapy, ultrasound, topical antibiotics, and cytokine growth factors. Electrical stimulation (ES) can provide therapeutic levels of electrical current may be delivered into the wound tissue from an external source. The external current may serve to mimic the failed natural bioelectric currents so that wound healing can proceed. Certain chemotaxic factors found in wound substrates contribute to tissue repair processes by attracting cells into the wound environment. Neutrophil, macrophage, fibroblast, and epidermal cells involved in wound repair carry either a positive or negative charge. When these cells are needed to contribute to autolysis, granulation tissue formation, anti-inflammatory activities, or epidermal resurfacing, ES may facilitate galvanotaxic attraction of these cells into the wound tissue and thereby accelerate healing.

In one implementations, surgical instrument is used to separate epidermis from skin at a donor site preferably of a same patient who has wound. Separated epidermis is processed by enzymatic cell separation to produce separated dermal cells which are dissolved to produce a dermal cell solution. Dermal cell solution is cultured onto plates to provide plated dermal cells and/or is split into dermal cell solutions (such as 70% confluency). Cultured dermal cells and dermal cell solutions are harvested, to be transferred to 3D printer cell dispensers such as dispenser. Following harvest of the donor site, individual cells of the epidermal layer are dissociated from the dermis. Dissociation of skin cells is accomplished by traditional trypsin: EDTA methods which is a preferable method for isolating keratinocytes from human skin. Human serum, bovine serum albumin, serum fibronectin, type IV collagen, and laminin are added to traditional cell culture media provide support to the fibroblasts and keratinocytes. These basement membrane protein constituents form the layers of the extracellular matrix on which these epidermal and dermal cells grow. Disassociated cells are incubated and continually shaken in cell culture flasks at 37° C. Cells are sub-cultured prior to confluency and allowed either to continue to proliferate in dissociated cell suspension flasks, plated on collagen plates to continue growth, or plated via the skin printer onto bovine collagen substrates.

In one embodiment, a bovine collagen matrix is augmented with growth factors such as Platelet-Derived Growth Factor (PDGF), epidermal Nitric Oxide Synthase (eNOS), Vascular Endothelial Growth Factor (VEGF), and Tumor Necrosis Factor Beta (TNF-beta). Low-dose insulin is added to also promote cell growth and proliferation. Insulin is used to improve wound healing and may be beneficial when used in an in vitro model to increase cell proliferation and would enhance cell proliferation into the collagen matrix.

3-4 days following the first application of autologous cells, and as the allogeneic cells and matrix begin to form obvious healthy epithelial tissue, lyophilized amniotic membrane (AM) is sprayed (such as from a modified airbrush-like apparatus (preferably associated with the print head of the 3D printer) onto the cell-seeded bovine collagen. There is a notable body of evidence to suggest that freeze-dried, powdered amniotic membrane promotes rapid healing and enhances the "take" rate of grafts. AM also inhibits natural inflammatory reactions which contribute to healthy tissue adhesion and structural development. There is evidence to suggest that combined with an electrical field, the application of AM will enhance cell migration and angiogenesis to cells located in the center-most region of the graft bed.

Continual layers of the cultured material are printed onto collagen plates until desired thickness is achieved. Amount of cells wanted in each layer, number of times the printer must create layers for the skin graft, intervals between applications, and types and amounts of growth factors and other ECM proteins to be added are factors.

As biofabricated hydrogel constructs for implantation usually have a lower stiffness than their target tissue, especially for use in the musculoskeletal system, improving stiffness of the hydrogel itself could be achieved by increasing the hydrogel crosslink density. In order to combine favorable biological and mechanical hydrogel properties, reinforcement of hydrogels has been achieved at different levels. Hydrogels have been reinforced by use of double networks and interpenetrating polymer networks (IPN), as well as by incorporation of nanoparticles, nanotubes or electrospun fibers. The crosslink density of the hydrogel could remain relatively low allowing for adequate tissue formation. However, most of these approaches will not be compatible with AM processes, since fabrication requires casting or a two-step crosslinking reaction. Therefore, recently multiple-tool biofabrication has been developed in which hydrogel constructs are reinforced by co-deposited thermoplastic polymer fibers by combining hydrogel and PCL in robotic dispensing and by combining electrospinning techniques with inkjet printing or laser-induced forward transfer printing. In this way, hydrogels can be processed at low polymer concentrations while shape and strength of the overall construct are secured by the thermoplastic polymer network. Moreover, it can be used in order to fabricate more complex shaped tissue constructs and the Young's modulus of the target construct can be tailored by adjusting the thermoplastic polymer network. Electrospinning produces a higher resolution of PCL fibers compared to robotic dispensing, and results in a network that better approaches the structure of natural ECM. Combining this technique with hydrogel deposition approaches will allow for the generation of reinforced hydrogel constructs with high control over the intricate spatial organization, although grafting between fibers and the hydrogel needs to be addressed in order to biofabricate truly integrated constructs. In addition, degradation kinetics of these hybrid structures should be understood and controlled. The hydrogel scaffold acts as a temporary environment and degrades as the embedded cells secrete proteases and subsequently produce extracellular matrix proteins that define the new tissue. In contrast, the polymeric reinforcement material should degrade in a significant slower rate, providing strength to the developing construct until the tissue has matured and at least once remodeled.

In one embodiment, photocrosslinkable interpenetrating polymeric network (IPN) of collagen and hyaluronic acid (HA) with precisely controlled structural and biomechanical properties. Both collagen and HA are present in crosslinked form in IPNs, and the two networks are entangled with each other. IPNs were also compared with semi-IPNs (SIPN), in which only collagen was in network form and HA chains were entangled in the collagen network without being photocrosslinked. Scanning electron microscopy images revealed that IPNs are denser than SIPNs, which results in their molecular reinforcement. This was further confirmed by rheological experiments. Because of the presence of the HA crosslinked network, the storage modulus of IPNs was almost two orders of magnitude higher than SIPNs. The degradation of the collagen-HA IPNs was slower than the SIPNs because of the presence of the crosslinked HA network. Increasing concentration of HA further altered the properties among IPNs. Cytocompatibility of IPNs was confirmed by Schwann cell and dermal fibroblasts adhesion and proliferation studies. We also fabricated patterned scaffolds with regions of IPNs and SIPNs within a bulk hydrogel, resulting in zonal distribution of crosslinking densities, viscoelasticities, water content and pore sizes at the micro- and macro-scales.

The pen can be used in the following exemplary applications:

Skin. In representative embodiments, to produce epidermal-like skin tissue, the following are printed:

(a) at least one cell type, and preferably at least two or in some embodiments three or four different epidermal cell types (e.g., keratinocytes, melanocytes, Merkel cells, Langerhan cells, etc., and any combination thereof); and/or at least one support compound such as described above (e.g., collagen, hyaluronic acid, elastin, keratin, etc., and any combination thereof); and/or (c) at least one growth factor as described above (e.g., basic fibroblast growth factor (bFGF), Insulin-Like Growth Factor 1, epidermal growth factor (EGF), etc., and any combination thereof);

In some embodiments the epidermal cells, support compound and/or growth factors printed as described above (which form an "epidermal" type layer) are printed on, or on top of, a previously formed (e.g., printed or ink jet printed) "dermal" type layer, the previously printed dermal layer layers comprising: (a) one, two, three or four different dermal cells (fibroblasts, adipocytes, mast cells, and/or macrophages), (b) at least one support compound as described above; and/or (c) at least one growth factor as described above.

Skin tissue produced by the method of the present invention is useful for implantation into or on a subject to, for example, treat burns, and other wounds such as incisions, lacerations, and crush injuries (e.g., postsurgical wounds, and posttraumatic wounds, venous leg ulcers, diabetic foot ulcers, etc.)

Bone. In particular embodiments, to produce bone tissues, the following are printed:

(a) at least one bone cell type, and preferably at least two or three different bone cell types (e.g., osteoblasts, osteoclasts, osteocytes, and any combination thereof, but in some embodiments at least osteoblasts and osteoclasts, and in some embodiments all three); and/or (b) at least one support compound such as described above (e.g., collagen, hyaluronic acid, hydroxyapatites, calicite, silica, ceramic, proteoglycans, glycoproteins, etc., and any combination thereof); and/or (c) at least one growth factor (e.g., bone morphogenetic protein, transforming growth factor, fibroblast growth factors, platelet-derived growth factors, insulin-like growth factors, etc., and any combination thereof).

Bone tissues produced by the processes described herein are useful for, among other things, implantation into a subject to treat bone fractures or defects, and/or promote bone healing.

Pancreatic. In representative embodiments, to produce pancreatic islet tissues, the following are printed:

(a) at least one, two, or three different pancreatic islet cell type (e.g., glucagon-synthesizing A (α) cells, insulin-producing B (β) cells, D (δ) cells, etc., and any combination thereof); and/or (b) at least one support compound such as described above (e.g., collagen, hyaluronic acid, proteoglycans, glycoproteins, elastin, etc., and any combination thereof); and/or (c) at least one growth factor (e.g., insulin-Like Growth Factor II (IGF-II), gastrin, transforming growth factor-alpha (TGF alpha), vascular endothelial growth factor (VEGF), etc., and any combination thereof)

Pancreatic islet tissue produced by the processes described herein is useful for, among other things, implantation into a subject to treat diabetes (including type I and type II diabetes).

Nerve. In representative embodiments, to produce nerve tissue, the following are printed:

(a) at least one, two or three cells types, and preferably (i) a central or peripheral nerve cells (e.g., cortical neurons, hippocampal neurons, dopaminergic neurons, cholinergic neurons, adrenergic neurons, noradrenergic neurons, etc., including any combination thereof), and/or (ii) at least one glial cell type (e.g., neuroglia, astrocytes, oligodendrocytes, Schwann cells, etc., including any combination thereof) and (iii) any combination thereof (e.g. a combination of at least one nerve cell and at least one glial cell); and/or (b) at least one support compound such as described above; (e.g., laminin, hyaluronic acid, collagen type IV, fibronectin, etc., and any combination thereof); and/or (c) at least one growth factor (e.g., NGF, brain-derived neurotrophic factor, insulin-like growth factor-I, fibroblast growth factor, etc., or any combination thereof); and any combination of the foregoing.

Nerve tissue produced by the processes described herein is useful, among other things, for implantation into a subject to treat nerve injury or degenerative diseases such as Parkinson's disease and Alzheimer's disease.

In some embodiments stem cells are printed onto substrates by ink-jet printing. Stem cells may be printed alone (typically in combination with a support compound or compounds) or in combination with one or more additional cells (e.g. in a combination selected to produce a tissue as described above). Stem cells (such as pluripotent or multipotent cells) are capable of differentiating into multiple different cell types or lines, including at least one of a hepatogenic-specific (or liver-specific) cell line, a myogenic (or muscle specific) cell line, an osteogenic (or bone specific) cell line, or an endothelial specific cell line. Useful cells for carrying out the invention include but are not limited to embryonic stem cells, parthenogenetic stem cells, amniotic fluid stem cells, and adipose-derived stem cells.

In general, AFSCs are cells, or progeny of cells, that are found in or collected primarily from mammalian amniotic fluid, but may also be collected from mammalian chorionic villus or mammalian placental tissue. The cells are preferably collected during the second trimester of gestation. In mice the cells are most preferably collected during days 11 and 12 of gestation. Preferably the mammalian source is of the same species as the mammalian subject being treated.

In general, the tissue or fluid can be withdrawn by amniocentesis, punch-biopsy, homogenizing the placenta or a portion thereof, or other tissue sampling techniques, in accordance with known techniques. From the sample, stem cells or pluripotent cells may be isolated with the use of a particular marker or selection antibody that specifically binds stem cells, in accordance with known techniques such as affinity binding and/or cell sorting. AFSCs used to carry out the present invention are pluripotent. Hence, they differentiate, upon appropriate stimulation, into at least osteogenic, adipogenic, myogenic, neurogenic, hematopoitic, and endothelial cells. Appropriate stimulation, for example, may be as follows: Osteogenic induction: The cKit+ cells are cultured in DMEM low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.); Adipogenic induction: To promote adipogenic differentiation, c-Kit+ cells are seeded at density of 3000 cells/cm2 in DMEN low glucose medium with 10% FBS supplemented with 1 μM dexamethasone, 1 mM 3-isobutyl-1-methylxantine, 10 μg/ml insulin and 60 μM indomethacin (all from Sigma-Aldrich); Myogenic induction: c-Kit+ cells were plated into Matrigel-precoated dish (1 mg/ml, Collaborative Biomedical Products) and cultured in myogenic medium (DMEM low glucose supplemented with 10% horse serum, and 0.5% chick embryo extract from Gibco) followed by treatment of 5 azacytidine (10 µM, Sigma) added in myogenic medium for 24 h; Endothelial induction: c-Kit+ cells are plated into gelatin-precoated dish and cultured in endothelial basal medium-2 (EBM-2, Clonetics BioWittaker) supplemented with 10% FBS and 1% glutamine (Gibco). In preferred embodiments no feeder layer or leukaemia inhibitory factor (LIF) are required either for expansion or maintenance of AFSCs in the entire culture process.

AFSCs also have substantial proliferative potential. For example, they proliferate through at least 60 or 80 population doublings or more when grown in vitro. In preferred embodiments AFSCs used to carry out the invention proliferate through 100, 200 or 300 population doublings or more when grown in vitro. In vitro growth conditions for such determinations may be: (a) placing of the amniotic fluid or other crude cell-containing fraction from the mammalian source onto a 24 well Petri dish containing a culture medium [α-MEM (Gibco) containing 15% ES-FBS, 1% glutamine and 1% Pen/Strept from Gibco supplemented with 18% Chang B and 2% Chang C from Irvine Scientific], upon which the cells are grown to confluence, (b) dissociating the cells by 0.05% trypsin/EDTA (Gibco), (c) isolating an AFSC subpopulation based on expression of a cell marker c-Kit using mini-MACS (Mitenyl Biotec Inc.), (d) plating of cells onto a Petri dish at a density of 3-8×103/cm2, and (e) maintaining the cells in culture medium for more than the desired time or number of population doublings.

Preferably, the AFSCs are also characterized by the ability to be grown in vitro without the need for feeder cells (as described in PCT Application WO 03/042405 to Atala and DeCoppi. In preferred embodiments undifferentiated AFSCs stop proliferating when grown to confluence in vivo.

AFSCs used to carry out the present invention are preferably positive for alkaline phosphatase, preferably positive for Thy-1, and preferably positive for Oct4, all of which are known markers for embryonic stem cells, and all of which can be detected in accordance with known techniques. See, e.g., Rossant, J., Stem cells from the Mammalian blastocyst. Stem Cells, 2001. 19(6): p. 477-82; Prusa, A. R., et al., Oct-4-expressing cells in human amniotic fluid; a new source for stem cell research? Hum Reprod, 2003.18(7): p. 1489-93.

In a particularly preferred embodiment, the AFSCs do not form a teratoma when undiferentiated AFSCs are grown in vivo. For example, undifferentiated AFSCs do not form a teratoma within one or two months after intraarterial injection into a 6-8 week old mouse at a dose of 5×106 cells per mouse.

In preferred embodiments the amniotic fluid stem cells used to carry out the present invention express several markers characteristic of ES cells and/or various multipotent adult stem cells. These include the transcription factor Oct-4 (Pou5f1), SSEA-1 (Stage Specific Embryonic Antigen 1), Sca-1 (Ly-6A/E), CD90 (Thy-1), and CD44 (Hyaluronate receptor. Ly-24, Pgp-1).

In preferred embodiments the amniotic fluid stem cells used to carry out the present invention do not express CD34 and CD105, markers of certain lineage restricted progenitors, nor the hematopoietic marker CD45.

In preferred embodiments the amniotic fluid stem cells used to carry out the present invention express low levels of major histocompatibility (MHC) Class I antigens and are negative for MHC Class II.

Differentiation of cells. "Differentiation" and "differentiating" as used herein include (a) treatment of the cells to induce differentiation and completion of differentiation of the cells in response to such treatment, both prior to printing on a substrate, (b) treatment of the cells to induce differentiation, then printing of the cells on a substrate, and then differentiation of the cells in response to such treatment after they have been printed, (c) printing of the cells, simultaneously or sequentially, with a differentiation factor(s) that induces differentiation after the cells have been printed, (d) contacting the cells after printing to differentiation factors or media, etc., and combinations of all of the foregoing. In some embodiments differentiation may be modulated or delayed by contacting an appropriate factor or factors to the cell in like manner as described above. In some embodiments appropriate differentiation factors are one or more of the growth factors described above. Differentiation and modulation of differentiation can be carried out in accordance with known techniques or variations of the above or below that will be apparent to those skilled in the art.

Pancreas. Differentiation of cells to pancreatic-like cells can be carried out in accordance with any of a variety of known techniques. For example, the cells can be contacted to, printed with, or cultured in a conditioning media Osteogenic induction: Cells may be induced to form bone cells by any suitable technique, such as culturing in DMEN low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.).

Adipogenic induction: Cells may be induced to promote adipogenic differentiation by any suitable technique, such as culturing in DMEN low glucose medium with 10% FBS supplemented with 1 dexamethasone, 1 mM 3-isobutyl-1-methylxanthine, 10 µg/ml insulin and 60 µM indomethacin (all from Sigma-Aldrich);

Myogenic induction: Cells may be induced to promote myogenic induction by any suitable technique, such as culturing in myogenic medium (DMEM low glucose supplemented with 10% horse serum, and 0.5% chick embryo extract from Gibco) followed by treatment of 5-azacytidine (10 µM, Sigma) added in myogenic medium for 24 h.

Endothelial induction: Cells may be induced to promote endothelial induction by any suitable technique, such as culturing in endothelial basal medium-2 (EBM-2, Clonetics BioWittaker) supplemented with 10% FBS and 1% glutamine (Gibco).

In another aspect, a collagen solution suitable for 3D printing onto the damaged skin is detailed. FIG. 5 shows an exemplary process for forming a wound healing solution. First, in 100, Deionized Water is placed in a vessel where batch has to be manufactured. Next, in 102, Carbomer, Allantoin, Dipotassium Glycerrhizate, and Disodium EDTA are added and mixed for 10-20 minutes. In 103, the remaining items in Table 1, except for Tiethanolamine, are added to the batch one by one. In 104, the batch is mixed for 5-10 minutes and Tiethanolamine is added with mixing. In 105, the batch is mixed for 5-10 minutes and the resulting collagen sample(s) can be taken for QC. Next, collagen is preferably phosphorylated with PX3 Phosphorus (Orthophosphoric Acid) which has the best binding capability to the collagen and shows the best results for the wound healing process. Phosphorylation is the metabolic process of introducing a phosphate group into the collagen's organic molecule. Orthophosphoric acid is the optimum material for different types of collagen in a controlled environment. Orthophosphoric acid is an inorganic acid. It is also known as phosphoric acid. The chemical structure of orthophosphoric acid is H3PO4, but these molecules can be re-combined to produce a number of compounds. Any derivatives of this acid are also referred to as phosphoric acids. The pure form of this acid is solid and white at room temperature. At 108.23° F. (42.35° C.), orthophosphoric acid will melt, resulting in a viscous, colorless liquid. At room temperature, this compound is typically anhydrous, which means it does not contain water. It has a polar molecular structure, however, which means that it is extremely soluble in water. As a chemical reagent, this acid is often converted into aqueous, or water-containing, solutions. These can have a potentiometric hydrogen ion concentrations (pH) ranging from 1.08 to 7.00, depending on the amount of acid present. An 85% solution of orthophosphoric acid is corrosive, but can be made non-toxic by way of dilution. Phosphate is a major intracellular anion which participates in providing energy for metabolism of substances and contributes to important metabolic and enzymatic reactions in almost all organs and tissues. Phosphate exerts a modifying influence on calcium concentrations, a buffering effect on acid-base equilibrium, and has a major role in the renal excretion of hydrogen ions.

Advantages of the composition and method for improving wound healing by administering either systemically or locally a therapeutic composition comprising phosphorylated collagen may include one or more of the following. The method provides for improved wound healing time, as well as a reduction in scar tissue formation and reduced loss of tissue function. The method will be particularly useful in cosmetic treatment have been shown here to increase the rate of wound healing by acceleration and enhancement of several key processes. The application of phosphorylated collagen has also been shown to result in decreased deposition of collagen at the final healed wound site which prevents loss of tissue function (strength) or cosmetic damage due to scarring.

The solution uses ingredients in Table 1 below:

nician utilizes a liposuction machine to extract a volume of adipose tissue via a needle or cannula. A variety of donor sites may be chosen for obtaining the adipose tissue such as, but not limited to, the abdomen, a thigh or the trochanteric area, or a knee.

The method includes processing or purification harvested adipose tissue to address prior tissue problems with large tissue transfer due to necrosis and other issues with transplanting adipose tissue with large amounts of triglycerides and mature adipocytes. During purification, a technician or operator places vial or other tissue containers containing the volume of harvested adipose tissue in a centrifuge (or other separation device). As shown, the centrifuge is operated or rotated for a period of time to separate water from the tissue and a large part of the triglycerides stored in the tissue. Both of these separated components are then removed from the vials (or, alternatively, the adipose tissue that has been separated from the water and triglycerides is removed for later injection into the patient). Interestingly, the purification method does not attempt to maintain mature adipocytes in a relatively undamaged condition, but it instead is designed to further damage a significant amount of these mature adipocytes in the adipose tissue to hasten their clearance by the patient's body after implantation. For example, the centrifugation (e.g., at rates in the range of about 1500 rpm to about 4000 rpm over a time period ranging from several minutes to about 20 or more minutes) may cause lesions in the thin cytoplasmic sheets of the mature adipocytes, which favors their rapid clearance after implant. Oil or other byproducts from these damaged adipocytes is also separated from the adipose tissue and is removed to leave a purified volume of adipose tissue (or the tissue is removed from the separated water, oil, and other byproducts). The operation of the centrifuge 164 and separation/isolation of the purified adi-

| Item | Ingredients | Purpose & Usage | % w/w |
|---|---|---|---|
| 1 | Deionized Water (Aqua) | Solvent | 61.05 |
| 2 | Sodium Hyaluronate | Moisturizing | 7.50 |
| 3 | Propylene Glycol & Camellia Oleifera Leaf Extract | Conditioning | 7.00 |
| 4 | Butylene Glycol | Humectant | 5.00 |
| 5 | Polysorbate 20 | Solubilizer | 3.50 |
| 6 | Propylene Glycol & Spiraea Ulmaria Flower Extract & Centella Asiatica Extract & Amino Acids | Conditioning | 2.50 |
| 7 | PEG-8 Dimethicone | Conditioning | 2.50 |
| 8 | Water & Imperata cylindrica Root Extract & Glycerin & PEG-8 & Carbomer | Conditioning | 2.00 |
| 9 | Collagen | Antiaging | 1.00 |
| 10 | Aloe Barbadensis Leaf Extract | Soothing | 1.00 |
| 11 | Carbomer | Viscosity Builder | 1.00 |
| 12 | Panthenol (Provitamin B5) | Conditioning | 1.00 |
| 13 | Water (Aqua) & Crithmum maritimum extract | Conditioning | 1.00 |
| 14 | Algae Extract & Mugwort (Artemisia Vulgaris) Extract | Conditioning | 1.00 |
| 15 | Phenoxyethanol-Methylparaben-Ethylparaben-n-Propylparaben-n-Butylparaben-iso-Butylparaben | Preservative | 1.00 |
| 16 | Sodium Ascorbyl Phosphate (Vitamin C) | Antioxidant | 1.00 |
| 17 | Triethanolamine | pH Adjuster | 0.50 |
| 18 | Water & Copper PCA & L-tyrosine & Glycine | Conditioning | 0.20 |
| 19 | Allantoin | Conditioning | 0.10 |
| 20 | Dipotassium Glycyrrhizate | Conditioning | 0.10 |
| 21 | Disodium EDTA | Chelating Agent | 0.05 |

Figure 2B:
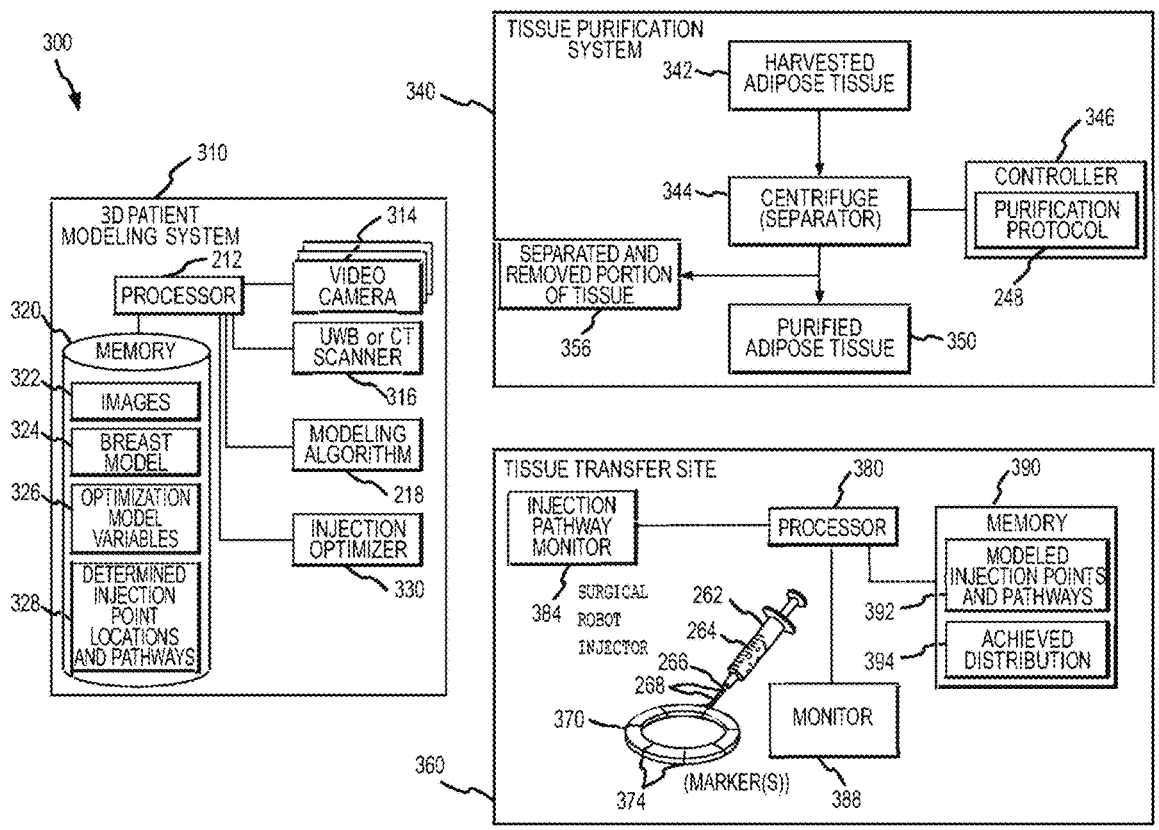
FIG. 2B shows an exemplary system for stem cell implantation into a patient with computer guidance and/or robots.

FIG. 2B shows an exemplary system for stem cell implantation into a patient with computer guidance and/or robots. The system applies a tissue transfer method that includes harvesting adipose tissue from a donor shown prone on a bed or support. In some preferred embodiments, the tissue transfer is an autologous tissue transfer and in these embodiments the donor is the same patient that is undergoing a breast reconstruction or augmentation. A physician or techpose tissue may be controlled automatically by a controller (e.g., a computer with a monitor as shown or other electronic device with a processor and memory) 168 that may store and later run one or more purification programs or protocols previously determined to provide a desired purification result.

The tissue transfer method also includes tissue transfer or deposition into the patient. The purified tissue from the processing 160 is believed to be better suited for successful implantation and acceptance for use in reconstruction and augmentation and, hence, all existing techniques for injecting and distribution of adipose and other cells/tissue may be used to implant the purified adipose tissue. In other embodiments, though, it is desirable to perform the transfer such that improved distribution is achieved. As will become clear from the following discussion, it is believed that more uniform distribution of the adipose tissue can be achieved through the use of computer-assisted modeling of the patient's breast (or other implantation site or area) and optimization of the location of injection points and injection pathways from such points (e.g., path length and angular trajectory from the point). Further, the positioning of the injection needle or cannula or the like can be monitored during the transfer to provide real time feedback to the physician and/or to determine whether the modeled injection points and pathways were utilized or followed during the transfer (e.g., to determine the actual points and pathways to determine the achieved tissue distribution in the patient). With this brief background in mind, the process 170 is shown to involve a physician 172 using a syringe filled with a volume of the purified adipose tissue 174 from process 160 to transfer the tissue 174 via needle or cannula 175 into a breast 113 of the patient 112. An injection guide 176 is positioned about the perimeter of the breast (or reconstruction/augmentation site or area) 113 to assist the physician 172 in identifying the injection points (see, also, FIG. 6 for more explanation of the use of an injection guide). The injection guide 176 may also be configured to provide the physician 172 with a reference (such as be in planar form marked with angular offset similar to a protractor) for injecting the tissue 174 along various injection pathways from each injection point. Alternatively, the injection points may be mapped and marked prior to the surgery or tissue transfer 170 to allow the physicians to locate the predetermined injection points. A control system 180 such as a computer with a monitor is provided to display the injection pathway model to the physician 172, and this may involve a three dimensional (3D) model of the breast 113 being displayed on the monitor along with all the injection points and their pathways or a "next" injection point and its pathways or a "next" pathway to be used by the physician 172 to sequentially perform the tissue deposition. A monitoring system 190 is provided with monitors/sensors 192 to track the progress of the process 170 such as by using X-Ray, MRI, IR, or other techniques along with optional markers on the guide 176 and/or needle 175 to allow the injection points and pathways actually followed by the physician 172 to be identified. In some embodiments, the injection tracking or monitoring includes provided real time imaging and display on the monitor of system 180 (or another monitor) and/or storing the information, which is later used to determine or generate a tissue deposition map that may show actual injection points and pathways and/or variance from the injection point and pathway model created prior to the procedure 170.

An embodiment of the tissue transfer of the present invention may be thought of as an autologous transplant of lipoaspirate (e.g., tissue such as adipose tissue harvested or aspirated via liposuction or similar methods from a patient). As noted, one of the significant uses of this inventive transplant method is for tissue regeneration in an area of a patient's body that is suffering from radiation-induced lesions following radiation therapy. To this end, FIG. 2B illustrates in functional block form that in addition to harvesting or obtaining a volume of adipose tissue that the transplant system or tools 200 includes a surface modeling system 210, a tissue purification system 240, and a tissue transfer system or site 260 with each including its own tools, devices, and systems for achieving a desired end function. Rather than using random injection or best judgment attempts to avoid clump injections, the surface modeling system 210 is used to generate a map or model of optimized injection points and pathways. To this end, the system 210 includes a processor or CPU 212 that receives and processes input from one or more cameras 214 and, optionally, a manual scanner or sensor 216. The camera 214 and sensor 216 may be used to obtain digital images 222 of the site to receive the implant such as breast that has undergone treatment for cancer and to obtain images 222 of a healthy breast such as the patient's breast that has not been treated for cancer. The images 222 are stored in memory 220 or otherwise made available to the processor 212. Alternatively, the images 222 may be obtained from other women or patients to obtain a digital image 222 of an area or surface to be reconstructed or augmented, e.g., to obtain images of a breast for which augmentation is being used to obtain or when a patient has had damage to both breasts and cannot provide images 222 for use in reconstruction. The processor 212 runs a modeling algorithm 218 to process the images 222 to generate a breast model (or model of another bodily area or surface to be reconstructed or augmented) such as by generating a mirror image of the patient's normal or undamaged breast or via manipulation of an existing breast as is known by those skilled in the reconstructive and cosmetic surgery fields for modeling bodily features after reconstruction or augmentation.

With the breast model 224 in memory 220, the processor 212 next runs an injection optimizer 230 that uses one or more optimization algorithms to process the breast model 224 and a set of optimization variables 226 to determine a set of injection point locations and pathways from such injection points 228 (as may be defined by length and angular trajectory from the injection point). The variables or parameters 226 may include a maximum number injection points to be utilized and a number of pathways from each point. Typically, the volume of tissue to be injected via each pathway is predetermine or fixed (e.g., such as the overall volume of purified tissue to be deposited or transferred divided by the number of injection pathways although, of course, the volume of tissue may be varied at each injection point and/or along each pathway to practice the invention and achieve a desired distribution in a breast).

The surface modeling system 200 provides computer-assisted, patient-specific planning of lipoaspirate surgical deposition. The planning or assistance is achieved with the mapped or determined injection point locations and defined pathways 228, which, as discussed above, are generated based on a computerized 2D or, more typically, 3D model of the body area to be treated. The model 224 is obtained by digital and calibrated photographs or images and/or laser scanning images from the cameras 214, scanner 216, or other equipment (not shown). Computer-assisted, pre-surgical planning of lipoaspirate deposition is designed to achieve near maximum uniformity of distribution and to limit significant overlaps and gaps in the tissue deposition. The process performed by the optimizer 230 is based on constrained optimization methods with the constraints or variables 226 in some cases including numbers and initial position of entry points, feasible length of insertion pathways (as a function, for example, of the length of the cannula(s) planned for use in the deposition and often based on the size of the bodily area being augmented or reconstructed), peak angular values of feasible insertion pathways, and, in some cases, inaccessible or untreatable areas. In some preferred embodiments, these variables 226 are patient specific and are selected by a physician or other technician to suit the particular patient and their needs and/or body shape and configuration (e.g., are entered into memory 220 as a step of the modeling process prior to optimization by the injection optimizer or algorithm 230).

Patient-optimized surgical planning carried out by the system 210 via running optimizer 230 may include minimizing or reducing a constrained objective function that is designed to minimize or limit dimension and variability of the areas generated by the intersection of tissue deposition pathways (see, for example, FIG. 6). The mapped injection model 228 produced is or may be used to generate a composite representation of the optimized entry point positions and directions of the insertion pathways from these points superimposed upon select patient images 222 and/or 3D digitized model 224 (again, see, for example FIG. 6). An advantage of the modeling system 210 and its implemented processes is that they make available an interactive optimization process for tissue deposition. For example, a technician or physician may interact with the system 210 during the creation of the model 224 to obtain a desired result after reconstruction or augmentation and also during selection or setting of the optimization variables 226 (e.g., changing the number of injection points, the number of pathways, or the like). Such pre-surgical planning can lead to standardization of the surgical procedure rather than relying on the judgment, experience, and skill level of the surgeon and can produce pre-surgical quantitative parameters. This ultimately reduces uncertainties in clinical outcomes between differing patients and produces patient-related quantitative documentation on the achievable accuracy in tissue deposition.

The system or set of tissue transfer tools 200 includes a tissue purification system 240 for processing or purifying adipose tissue prior to use for an implant. As shown, harvested adipose tissue 242 is provided to or positioned in a separation device such as a centrifuge 244. The centrifuge 244 may be manually operated or run automatically by a controller 246 based on a purification protocol 248 (e.g., a program defining one or more centrifugation speeds and times). During this processing, a portion of the tissue such as water, oil from damaged mature adipocytes, triglycerides, and other components, separate from other adipose tissue. This volume or portion is removed 256 leaving a volume of purified adipose tissue 250. For example, the protocol 248 may define a harvested volume to be inserted into each reservoir or vial in a centrifuge 244, a revolution rate at which to run the centrifuge, and a time period. After the time period ends, the separated, undesired portion 256 is removed from each reservoir or vial in the centrifuge 244. Alternatively, the protocol 248 may define a stepwise procedure and define volumes of the separated tissue 256 to be removed at each step (e.g., run the centrifuge at a first speed, remove a particular volume of separated tissue 256, run the centrifuge at a second speed, remove another volume of tissue 256, and so on) or such removal may be handled automatically with some centrifuges 244 or separation devices being configured to selectively remove the separated tissue 256 or to remove the purified adipose tissue from a "ring" in the centrifuge reservoir or vials (e.g., based on expected location of the purified adipose tissue 250 based on centrifugal rates and densities of the tissue 250).

Significantly, in addition to harvesting the adipose tissue, the procedure for procurement and treatment of autologous (or other donor) adipose tissue or lipoaspirate includes purifying the tissue. The lipoaspirate purification procedure is generally designed to remove a large part of the triglyceride stored in the harvested adipose tissue. The purification by centrifugation or similar techniques also functions to cause lesions in the thin cytoplasmic sheets of mature adipocytes in the harvested adipose tissue. In other words, the purification includes intentionally causing additional damage to the adipocytes that have been traumatized by liposuction or harvesting processes, and this additional damage is preferably to the point of one or more lesions so as to enhance the speed at which a treated patient is able to clear the damaged mature adipocytes after implant. In some preferred embodiments, purification is obtained by centrifugation carried out, in part, to separate a set of adipose tissue (i.e., the purified adipose tissue) from its water content and from the oil produced by the destruction of the damaged adipocytes. An advantage of use of the inventive purification technique is that there is no need for any kind of cell culture to grow additional tissue outside the patient's body as was common with many other tissue implant techniques, and avoiding culturing better controls risks of micro-organism contamination, reduces the complexity of the tissue preparation process, and controls or limits associated costs. A further advantage of the purification or tissue preparation process is that by the process does not require the technically challenging step of isolating or extracting adipose-derived stem cells (ADAS) but instead allows the ADAS to remain in their natural support structure or 3D scaffold which facilitates vascularization and other benefits.

The system 200 also includes a tissue transfer site or system 260. The system 260 includes a processor or CPU 280 that acts to provide computer assistance to a physician during or before tissue transfer. The processor 280 functions to access memory 290 and to display a distribution model such as by displaying on the monitor 288 (or providing a hard copy) the modeled injection point locations and pathways 292 or superimposing this information 292 upon a 3D or 2D model of a breast or other portion of a patient's body. As shown, the tools or system 260 includes an injection guide 270 with indicators 274 showing modeled injection points to provide a reference point and plane for performing the injections. The injections or tissue transfer is performed in this case with a syringe 262 or similar device that contains a volume of purified adipose tissue 264 from purification system 240. Using the modeled injection distribution on the monitor and the guide 270 a physician (not shown) performs the tissue deposition by inserting the needle or cannula 266 at each injection point (e.g., points marked or referenced on the patient or by indicators 274 of guide 270) and attempting to follow defined pathways. An injection pathway monitor 284 is provided to determine such as by identifying the location of a marker(s) 268 on the needle 266, the pathways actually used by a physician during tissue deposition or transfer. This information from the injection pathway monitor 284 may be stored with or without further processing by processor 280 as shown by achieved distribution data 294 in memory 290. With the tissue transfer site or set of tools 260, the system 200 provides computer-assisted, intra-surgical guidance for lipoaspirate deposition. The pre-surgical plan including the injection points and pathways 292 provides the surgeon with the map for intra-operative guidance or aiming to achieve a high level of uniformity of adipose tissue deposition, which is typically purified adipose tissue but the pre-surgical plan would benefit nearly any tissue transfer or implant such as unpurified adipose tissue, adipose tissue with additional stem cells, or other tissues/cells (e.g., mesenchymal cells, especially smooth or skeletal muscle cells, myocytes (muscle stem cells), chondrocytes, adipocytes, fibromyoblasts, ectodermal cells, or nerve cells which may or may not be dissociated). Further, growth factors, angiofactors, anti-inflammatories, selective growth inhibiters, and the like may also be provided with or after implantation of the tissue. Tissue and cells are preferably autologous cells, obtained by biopsy and expanded in culture, although cells from close relatives or other donors may be used such as with appropriate immunosuppression. Immunologically inert cells, such as embryonic cells, stem cells, and cells genetically engineered to avoid the need for immunosuppression may also be used. Yet further, tissue expanders may be useful in some applications but are generally not a required tool for use with the present tissue transfer method.

A specific interactive tool such as the system 260 allows an operator to select (such as via a mouse, a keyboard, a touch screen, by voice command or other user interface or user input device) a specific entry or injection point and pathway at that point and to proceed pathway-by-pathway and point-by-point to complete the network of predefined pathways (such as via a display of model 292 via processor 290 on monitor 288). Additional features of the tool set 260 include the monitor 284 that may be used by the processor to provide a surgical navigation system for guiding the surgeon during cannula 266 insertion. Such a monitoring system 284 may be based on an optical IR real-time tracking device, which provides the 3D position of the cannula 266 (e.g., carrying a configuration of IR reflecting markers 268 or the like) with respect to the stereotactic patient-mounted reference frame or model shown on the monitor 288 upon which the surgical plan 292 may also be superimposed or mapped. In this embodiment, a real-time graphic feedback is generated on the displayed surgical plan (e.g., tissue transfer distribution mapping) at the computer screen 288 providing information on the current deposition direction and, in some cases, signaling deviation with respect to the planned trajectory or pathway and, in some further embodiments, providing a related correction. The intra-operative method ensures improved accuracy in transferring the planned injection points and pathways 292 into the reality of the surgical procedure and also produces specific quantitative documentation 294 describing the actual geometry of lipoaspirate that the operator or surgeon was able to achieve for the particular patient.

FIG. 3 illustrates generally the steps of a tissue preparation process 300 that starts at 305 and is used to prepare a volume of adipose tissue for implanting or deposition in a patient such as for augmentation or for reconstruction of soft tissue after removal and/or radiotherapy. The method 300 continues at 310 with the selection of a donor and donor site. As noted above, the tissue is typically autologous tissue but this is not a requirement of the invention. In step 310, a donor site for obtaining adipose tissue is selected such as the medial area of the knee, the abdominal region, the trochanteric, or other regions of the donor's body. At 320, the donor site is prepared for harvesting such as by infiltrating the selected region with a cold saline solution with the addition of adrenaline (e.g., 10 to 20 cubic centimeters (cc)) and lidocaine (e.g., 20 to 30 cc of lidocaine 0.5% per 500 cc or the like). At 330, a volume of adipose tissue (e.g., up to 2 or 3 cc of adipose tissue or more) is removed such as by using a cannula (e.g., a 2 mm or other diameter cannula) and a syringe.

At 340, the harvested adipose tissue is transferred to a centrifuge for centrifugal separation or purification such as by placing a plurality of syringes directly in the centrifuge or transferring their contents into different reservoirs or vials. In some embodiments, the operator is allowed to select a purification protocol from a set of previously determined useful protocols while in other cases a default or preferred protocol is set or fixed for use in all purification steps 350. In some cases, for example, the protocols may include (but are not limited to): (a) a spin speed or centrifuge rate of about 1900 rpm for a spin time of about 15 minutes; (b) a spin speed of about 2700 rpm for about 8 minutes; (c) a spin speed of about 2700 rpm for about 15 minutes; (d) a spin speed of about 3500 rpm for about 8 minutes; and (e) a spin speed of about 3500 rpm for about 15 minutes. More generally, the protocol may be thought of as operating the centrifuge at a spin speed and for a spin time predetermined to obtain substantial separation of water from the tissue, oil from the damaged mature adipocytes, triglycerides, and/or other undesired components and the spin speed typically is in the range of about 1000 rpm to about 4000 rpm or higher but more typically between about 1900 rpm and about 3500 rpm and the spin time ranges from several minutes to about 30 or more minutes but more typically is in the range of about 8 minutes to about 15 minutes. The preferred protocol is generally one in which achieves substantial removal separation of the oil upon causing lesions in a significant percentage of the mature adipocytes and separation of substantial triglycerides while retaining structural integrity of stem cells (e.g., maintains cell viability of ADAS to a large degree). At 360, the centrifuge loaded with the harvested adipose tissue is operated based on the selected or default protocol. At 370, the separated oil, water, triglycerides, and/or other components or tissue separated from the adipose tissue is removed to generate a smaller volume of purified adipose tissue (e.g., tissue composing or being rich in ADAS). The purified adipose tissue is, at least temporarily, stored or packaged in step 380, for later transfer to a patient (e.g., the donor), and the process 300 ends at 395. The overall volume of purified adipose tissue may vary widely to practice the invention and typically with each patient. As an example, the average size of a breast implant is in the range of about 325 to about 400 cc, and it may be desirable to prepare up to about 400 cc or more of purified adipose tissue to perform a breast reconstruction after a full mastectomy followed by radiography treatment.

FIG. 4 illustrates exemplary steps of a tissue transfer or deposition process 400 of the present invention that starts at 405. At step 410, the area of the patient (e.g., one or both of the patient's breasts) that is being augmented or reconstructed after loss or damage of soft tissue such as adipose tissue it modeled. Such modeling 500 is shown relatively generally in FIG. 5 and includes obtaining one or more photographs of the area such as of the area to be reconstructed or augmented 518 and a reference area 514 (e.g., the patient's other breast). In some cases, a manual or laser scanner may be used instead of the photographs or in addition to the photographs to obtain a plurality of data points 510 indicative of the 3D topography of the reference breast or area 514 and the area to receive the implant 518. The image is digitized as shown at 520 to provide a digital image or plurality of data points of the reference area 524 and of the implant area or site 528. Interpolation, filtering, and rendering are used to generate a more complete computer model of the reference breast or area and of the area to be augmented or reconstructed as shown at 530. Then, texturing and other processing is performed to achieve a 3D model or virtual version 540 of the breast to be reconstructed or augmented 548, which is typically the desired or final form for the breast or body area and may be a mirror image of the reference breast or area or may be a modeled or textured model or plan for the breast or area being reconstructed or augmented.

At 420, the method 400 continues with entering distribution optimization parameters or variable values or alternatively accepting one or more default values. The parameters or variables typically include at least a number of injection points and a number of injection pathways at each injection or entry point. The parameters may also include a maximum length of the pathways and can sometimes include a maximum or peak angle for the pathway. At 420, the method 400 continues with processing the modeled breast or tissue injection surface from step 410 using the optimization parameters of step 420 to define preferred or "optimized" injection pathways from a set of injection points, with the injection point locations also being defined. The model or planned injection mapping/network is stored in memory, and at 440 is provided to a physician for use in performing tissue transfer or deposition. The model is typically overlayed or superimposed on the modeled breast from step 410, and the model is often provided on a computer or other monitor in the operating room. At step 450, an optional injection guide is positioned on or near the patient such as about the perimeter of the breast or other area to be reconstructed or augmented. The guide is optional as in some cases it is preferable to mark or otherwise identify the injection points from the model on the implant site. At 460, the pathway model is used to inject a volume of purified adipose or other tissue at each injection site and along each defined pathway. Step 470 is optional and provides for monitoring of the tissue transfer or injection of step 460 to provide injection guidance and/or verification/documentation of actual tissue distribution. The monitored or detected injection pathways and the modeled tissue distribution (calculated actual distribution) may then be stored in computer memory at 480, and the process 400 ends at step 495.

FIGS. 6 and 7 provide an illustration of an exemplary injection pathway model 610 as may be displayed on a monitor or otherwise presented to an operator or surgeon and is shown when in use with an injection guide 620 with injection point indicators or reference lines 622. A plurality of injection points 630 are spaced apart about the periphery of the implant area (e.g., a patient's breast). As shown, the points 630 are not equally spaced but instead have been located in a more irregular pattern by the optimization algorithm to achieve better distribution. Also, the periphery or outline defined by the points 630 is shown to be relatively circular, oval, elliptical or the like but often the periphery will be an irregular shape. As shown, the optimization parameters include a number of points of seven and the number of injection points at each point was set at four. Of course, smaller or larger values may be used for each of these parameters or variables. Also illustrated in FIGS. 6 and 7 is the feature that the travel pathways 634 do not necessarily have equal lengths and injection by the surgeon at each pathway may require a reference marking on the needle/cannula or differing length needles/cannulas to match these lengths. Further, each of the injection pathways 634 is spaced apart and is defined by a corresponding trajectory angle (positive or negative) from the injection or entry point 630 which may be relative to a plane passing through the injection point horizontally and vertically (e.g., a 3D trajectory path is defined for each pathway), and, in some cases, the guide 620 provides the horizontal reference plane for the trajectory pathways 634.

In one embodiment, the computer optimization algorithm performs multi-parametric optimization through non-linear, unconstrained minimization (e.g., in a projective 2D version). Input in this case may be the surface model of the implant area or site, the number of entry points (e.g., 3 to 10 or more), the number of paths per entry point (e.g., 1 to 5 or more), and pathway length (e.g., a fixed length for every pathway in some embodiments). The output of the program or algorithm is the entry point position on the surface model (e.g., on the patient's implant site) and the path directions for all the injection points. The function cost is typically made of: the number of areas in which the paths overlap (to be maximized in most cases), the area dimensions (to be minimized in most cases), and the area variability (to be minimized in most cases). In practice, the algorithm generally works by starting from an initial guess and then iteratively searching for the "best" position with respect to the model of the implant site surface for: entry points, path direction, and, in some cases, path length. In some preferred cases, the "best" position is selected in order to maximize the number of areas formed by the intersections of the injection pathways and to minimize their absolute size and size variability (i.e., homogeneity).

One bio-printing embodiment places human cells down and then either print sequentially or with a second print head in parallel places a support material with a biocompatible gel that minimizes tissue rejection. This support material can be a hydrogel, scaffold or other varieties of material. Hydrogels are polymeric compounds with a hydrophilic structure similarly to that of hyaluronic acid (HA). HA is an important molecule to living beings. In that, it is a multifunctional high molecular weight polysaccharide found throughout the animal kingdom, especially in the extracellular matrix (ECM) of soft connective tissues. HA is thought to participate in many biological processes, and its level is markedly elevated during embryogenesis, cell migration, wound healing, malignant transformation, and tissue turnover. The enzymes that degrade HA, hyaluronidases (HAases) are expressed both in prokaryotes and eukaryotes. These enzymes are known to be involved in physiological and pathological processes ranging from fertilization to aging. Hyaluronidase-mediated degradation of HA increases the permeability of connective tissues and decreases the viscosity of body fluids and is also involved in bacterial pathogenesis, the spread of toxins and venoms, acrosomal reaction/ovum fertilization, and cancer progression. Furthermore, these enzymes may promote direct contact between pathogens and the host cell surfaces. Depolymerization of HA also adversely affects the role of ECM and impairs its activity as a reservoir of growth factors, cytokines and various enzymes involved in signal transduction. Inhibition of HA degradation therefore may be crucial in reducing disease progression and spread of venom/toxins and bacterial pathogens. Hyaluronidase inhibitors are potent, ubiquitous regulating agents that are involved in maintaining the balance between the anabolism and catabolism of HA. Hyaluronidase inhibitors could also serve as contraceptives and anti-tumor agents and possibly have antibacterial and anti-venom/toxin activities. Additionally, these molecules can be used as pharmacological tools to study the physiological and pathophysiological role of HA and hyaluronidases.

In one embodiment, the production of functional human tissue can be as follows:

select particular cell for particular organ requirements
create "bio-ink" from cultured cells, and insert into a bio-print head component form HA hydrogels with synthetic or cross-linked materials in the core and surrounded by lightly cross-linked HAs or non-cross-linked HA to reduce risk of tissue rejection place slow release drug modules containing Ciprofloxacin or suitable antibiotic keeps tissue reaction in control for about six months to minimize tissue rejection and tissue scarring buildup cells are then layered among the HA hydrogels until the tissue is produced
- layers in-between HA act as structural support for tissue growth
- "supportive scaffold materials" include HA, fibrin and collagen hydrogels
- hydrogels fill up spaces in-between the layers and as structural support and fuse different cell samples to create larger tissues
- build vascularization with stem of arteries, capillaries, and veins that support the organ to deliver nutrients and remove waste created by the cells
- place slow release drug modules containing ECM suppressant to control tissue reaction for about six months to minimize tissue rejection and tissue scarring buildup In one embodiment, the printer creates blood vessels distinct layers or tunics. The tunics surround the central blood-containing space with an innermost tunic (Tunica Intima) with a smooth, friction reducing lining and an outermost layer(Tunica Externa) composed of loosely woven collagen fibers that protect the blood vessel and anchor it to surrounding structures. Optionally, for blood transport, a mid layer (Tunica Media) can be formed with muscle cells that contract and relax, and the elastin allows vessels to stretch and recoil.

To minimize tissue rejection, a biodegradable layer on 3D-printed implant is designed to act as a switch to turn on the release of an ECM suppressing therapeutic agent (i.e. fluoroquinolone, glucosamine, diethylcarbamazine, etc.) once enough proliferation has occurred to encapsulate the implant implant or when ECM deposition begins. Exemplary fluoroquinolones include ciprofloxacin, levofloxacin, and moxifloxacin. The drug can be ciprofloxacin which is an antibiotic in a group of drugs called fluoroquinolones. In one embodiment, the Cipro can be sprayed or otherwise atomized onto the 3D-printed implant surface. In another embodiment, the implant can be submersed in a solution with Cipro and a binder can be provided to bind the Cipro to the implant. Ciprofloxacin fights bacteria in the body. Ciprofloxacin is used to treat different types of bacterial infections. It is also used to treat people who have been exposed to anthrax. Other medications can be used, for example, leukotriene receptor antagonists, such as zafirlukast (Accolate®), montelukast (Singulair®), and pranlukast administered orally can moderate the capsular contracture. Other medications include antibiotics surrounding the implant. Finally, textured implants have yielded a reduction in capsule formation.

The method can include timing the switch to match the typical time (Encapsulation Development Time) for development of tissue encapsulation (timing approach) or to have the encapsulation event itself trigger the switch (event triggered approach).

Under the timing approach, a biodegradable layer can be coated on the therapeutic agent matrix that would degrade enough to allow therapeutic agent elution around 20 to 40 days, the typical time of tissue encapsulation of an implant implant. The layer could be configured to degrade in tissue and/or in blood. For the switch to be effective, it must effectively block ECM suppressing therapeutic agents from eluting for the duration of Encapsulation Development Time and then quickly turn on to fully elute a therapeutic agent to block proteoglycans (i.e. versican, decorin, biglycan), hyaluronan, inter-a-trypsin and/or collagen (types I and III) from being further synthesized and deposited. In this way significant ECM-related restenosis is prevented since proteoglycans and collagen are the dominant components of ECM. The ECM is responsible for the bulk of restenosis in the long term.

Since the typical ECM suppressing therapeutic agent (i.e. fluoroquinolone) is hydrophilic, a good solid barrier layer should be made of a hydrophobic or slightly hydrophobic substance to control the elution time and degradation time to better match the Encapsulation Development Time. This outer barrier layer of a more hydrophobic substance can be selected from polylactic acid (PLA), polyglycolic acid (PGA), a copolymer of PLA and PGA (PLGA), polycaprolactone (PCL), other biodegradable polyesters, polyamino acids, or other hydrophobic, biodegradable polymers.

Preferably, under the barrier layer and immediately adjacent to the therapeutic agent matrix layer another layer is provided that is instead slightly hydrophilic or closer in polarity to the therapeutic agent itself than the outer barrier layer. This middle layer is the key to the rapid, burst characteristic of therapeutic agent elution while the outer barrier layer is the key to the delayed onset characteristic of therapeutic agent elution.

As an alternative or as a complement to providing a separate layer beneath the barrier layer that is opposite in polarity to the barrier layer and closer in polarity to the therapeutic agent, the material used to form the therapeutic agent soluble material can be provided in pockets distributed throughout the barrier layer. By interspersing the barrier matrix with pockets of a hydrophilic substance (i.e. dextran, heparin) a switch effect for accelerated barrier layer degradation and therapeutic agent elution can be better achieved. Upon a threshold level of water penetration into the barrier matrix containing the pockets, the pockets increase in pressure to the point where they burst to destroy the barrier structure. The pockets act as isolated reservoirs or oases for hydrophilic physiologic and other fluids that the barrier layer's base material does not readily accept. Although the biodegradation of the barrier layer may be directed by other means such as the emergence of a restenotic environment in which the barrier layer dissolves, the incorporation of pockets allows additional options for fine-tuning the timing of barrier degradation by also making it indirectly susceptible to hydrophilic fluids and environments.

If the therapeutic agent happens to be hydrophobic rather than hydrophilic the polarities (hydrophobicity and hydrophilicity) of the respective matrices, layers, and/or pockets should be reversed. The bottom line is that the outermost barrier layer is to be opposite in polarity to the therapeutic agent and the inner layer(s) or pocket(s) that are closer to the therapeutic agent are closer in polarity to the therapeutic agent. However, preferably the therapeutic agent itself is contained in a matrix that is opposite in polarity for stabilization. The design is sandwich-like in configuration with the outer barrier and the therapeutic agent matrix analogized to pieces of bread between the unique opposite polarity inner layer or pockets analogized to the meat. The inner opposite polarity layer is the trigger to burst elution because the therapeutic agent easily dissolves within it suddenly and completely.

Under the event triggered approach, there are several ways to trigger the switch to allow therapeutic agent elution to occur upon tissue encapsulation of the implant:

1. First, the coating covering the therapeutic agent matrix is designed to immediately break down to allow therapeutic agent elution upon tissue encapsulation. This can be achieved by coating the therapeutic agent matrix with a slightly to hydrophobic, biodegradable outer barrier layer that breaks down quickly upon the presence of a slightly to very hydrophobic environment such as provided by restenotic material. A thin layer of wax or a fatty substance exemplify the type of coating to be used. Specific examples of these include lipoprotein, collagen, polyamino acids, PLA, PLGA, and polycaprolactone, 2. Second, the ECM suppressing therapeutic agent can be bound to a molecule that inactivates the therapeutic agent until ECM factors (i.e. collagen, proteoglycans) are present.

3. Third, the switch can be turned on by other factors accompanying tissue encapsulation or extracellular matrix thickening including: hormones, enzymes, and/or peptides, etc.

4. Fourth, pressure can be used to induce release of the therapeutic agent, i.e. by housing the therapeutic agent within a semi-permeable membrane that bursts or by including pressure-building pockets within a barrier layer.

5. Fifth, pH changes can be used to induce release of the therapeutic agent if the material retaining (i.e. coating or serving as a matrix for) the therapeutic agent is sensitive to acids or bases and degrades (in tissue or in blood) upon being subjected to acidic or basic environments. In one embodiment, the therapeutic agent is coated with a slightly hydrophobic, acid-sensitive layer of PLGA. Tissue encapsulation of the implant implant can trap the PLGA and the acids produced from PLGA degradation. Subsequently, the concentration of acids is dramatically increased which leads to rapid degradation of the PLGA itself.

This event triggered approach offers a high degree of control of therapeutic agent elution and/or activation. The onset of therapeutic agent elution and/or the catalyst for therapeutic agent activation is particularized to occur independently and exclusively on the implant localities encapsulated by tissue while the elution is restrained and/or the therapeutic agent remains dormant and inactive on the implant localities that are still bare and unencapsulated. Encapsulation rates vary between procedures, individuals, and implant localities. Therefore, event-triggered therapeutic agent control provides an individualized approach for enhanced accuracy, safety and effectiveness.

It is preferred that the dosage of the anti-restenosis therapeutic agent is higher at the ends of the implant to compensate more aggressive restenosis at the ends of the implant.

In one embodiment, the present invention uses aligned nanofibers and/or aligned nanogrooves to form the implant coating to create an artificial functional endothelial layer that will attract the deposition of a natural endothelial layer. The natural endothelial layer is composed of aligned, elongated endothelial cells that will align themselves amongst the aligned fibers and deposit directly on the implant itself even when the aligned nanofiber coating is not loaded with any specifically reactive linking agents.

The xenographic/xenogenic artificial functional endothelial layer of aligned fibers and/or aligned grooves may be composed of or seeded with synthetic materials, allogeneic materials (cells or clones from a second subject of the same species as the patient), and/or heterologous materials (cells or clones from a second subject not of the same species as the patient). In any case, the aligned geometry of the artificial functional layer paves the way for the growth of a natural functional layer of autologous endothelial cells produced in vivo that will encapsulate the implant implants and injured to tissue to a depth of 0.1 mm thereby masking its xenographic (foreign) nature to preclude an immune response that may cause thrombosis.

One embodiment addresses LST without sacrificing the effectiveness of using restenosis suppressing therapeutic agents to avoid late stage restenosis and using ECM regulating therapeutic agents to reduce thickening of the ECM. This is done by depositing a biodegradable layer of aligned microfibers (AMF), aligned nanofibers (ANF), and/or aligned grooves (AG) on top of a DES as an effective means to delay the onset of release of one or more therapeutic agent (i.e. restenosis or ECM inhibitory therapeutic agents) as well as to facilitate endothelization. This way the patient benefits from two desired characteristics:

1. the safety of the BMS by having a smooth endothelium or neointima encapsulating the implant implants; and 2. the long term effectiveness of proven DES (such as Cypher and Taxus) by maintaining delivery of a local restenosis and/or ECM suppressing therapeutic agent from the implant but with a delayed onset.

The AMF/ANF/AG material may take the form of a coating, a matrix, or an implant body so long as its structure and orientation are such that it can both facilitate endothelization and also delay the onset of therapeutic agent release, if therapeutic agents are used. Preferably, the AMF/ANF/AG material lasts for 15-30 days before it is fully degraded to expose the therapeutic agent underneath. However, it may work by fully degrading anywhere between 5-60 days. The AMF/ANF/AG material is preferably made of PGA or a copolymer of PGA-PLA. These are proven compounds used on DES as well as biodegradable sutures and are well documented for their compatibility with blood. PGA and PGA-PLA are especially well suited to degrade within 15-30 days. The delay time before onset of release of the ECM suppressing therapeutic agent (i.e. fluoroquinolone, glucosamine, diethylcarbamazine, etc.) is equal to the time it takes the AMF/ANF/AG material to fully degrade. This delay time is controlled by the exact chemical compounds used to create the coating and also the coating thickness. For example, since 50% PLA:50% PGA degrades more quickly than a 75% PLA:25% PGA mix, to obtain the same therapeutic agent release onset delay a thicker layer of 50% PLA:50% PGA would be used than if a 75% PLA:25% PGA mix were used. The AMF/ANF/AG material is preferably between 0.1 micron and 20 microns thick.

Alternatively, instead of PGA and/or PLA, the AMF/ANF/AG material can also preferably be made of poly(ethylene glycol) (PEG), also known as poly(ethylene oxide) (PEO) or polyoxyethylene (POE). Caprolactone (CPL) can also be used. CPL and PEG are elastomeric materials and if the AMF/ANF/AG medical device has elastomeric properties it will better conform to the natural shape of the lumen in which it is inserted or implanted. Elastomeric materials are better able to close gaps between an implant wall and a lumen wall. Avoiding incomplete apposition of the implant implants against the lumen wall reduces the formation of stagnant pockets in which a thrombus is more likely to develop. Metallic implant implants are typically stiff and cannot conform well to the lumen when the lumen is not smooth and uniform, as is often the case. However, an elastomeric coating upon non-elastomeric implant implants ameliorates this problem by flexing, bending, expanding, and contracting to occupy the differential spaces created by the nonconformity between the lumen wall and the implant implants. Alternatively, if the implant implants themselves are made of AMF/ANF/AG elastomeric materials they can directly model the irregular surface patterns of anatomic lumens.

The AMF/ANF/AG material can also be made out of biological molecules (biomolecules) such as collagen, fibrin, or fibrinogen. Various other substances that can be used to form the AMF/ANF/AG material are: phosphorylcholine, nitric oxide, high density lipoprotein, polyzene-F, PTFE polyetherester, hydroxyapatite, polyhydroxy-butyrate, polycaprolactone, polyanhydride, poly-ortho ester, polyiminocarbonates, polyamino acids, and polyvinyl alcohol.

Irrespective of the chemical components used to form the AMF/ANF/AG material, when used as a delay coating the AMF/ANF/AG material is preferably negatively charged and also preferably has a nitric oxide functional group. Thus, as the fibers degrade, nitric oxide is released. Within the bloodstream of the lumen occupied by the implant, the nitric oxide serves to further inhibit restenosis by preventing platelet aggregation and macrophage/leukocyte infiltration, reducing smooth muscle cell proliferation, and decreasing inflammation generally while aiding the healing process. An aligned coating with a nitric oxide group (ANO) on an implant (or other intravascular medical device) forms an artificial endothelium layer due to the smooth, streamlined surface the aligned fibers/grooves provide coupled with the ability of nitric oxide to prevent aberrations on this smooth surface as the fibers degrade.

The inventor recognizes the use of any biocompatible materials that can be formed into aligned nanofibers, aligned microfibers, or aligned grooves for the AMF/ANF/AG material used to form an implant, a coating, or a matrix for therapeutic agent(s). The present invention also recognizes the ability to use the AMF/ANF/AG material in conjunction with other coatings, layers, matrices, pores, channels, reservoirs, etc. to delay onset of the release of any therapeutic agent and/or to encourage structured (i.e. aligned) endothelization.

The present invention also teaches the criticality of matching the time period of delay prior to therapeutic agent release with the time it takes for the AMF/ANF/AG implant surface to become covered (i.e. encapsulated) by endothelization to a depth of approximately 0.1 mm. The artificial functional endothelium layer itself is a very thin (i.e. only one or a few cells thick). A thin layer does not burden the implant with unnecessary volume (i.e. on the periphery of a cross-section) that could make insertion and adjustment within the lumen more difficult. A thin layer also does not significantly reduce the inner diameter of the implant's lumen and therefore does not interfere with hemodynamics or obstruct blood supply to a treated area.

When the implant is not formed of a material (i.e. such as an elastomeric aligned material) that enables it to conform to the shape of a lumen surface, a thrombus is more likely to develop causing a localized inflammatory reaction. Also, when the implant doesn't conform well to the shape of a lumen, the process of restenosis cannot be effectively controlled. Although systematic therapeutic agents administered with BMS and therapeutic agents supplied by DES can slow or modulate the rate of ineffective restenosis they are not typically used to encourage a moderate amount of beneficial restenosis. Any restenosis that does occur in a vessel having an uneven surface with implant implants that inadequately conform to the natural cell and protein structure (and/or shape) of the vessel is likely to be uncontrollable and problematic. Smooth muscle cell migration and proliferation is likely to form the first tissue layer over the implant implants. In contrast, the present invention provides a preformed artificial functional endothelial layer to provoke a first in vivo layer of natural endothelial cell growth.

According to the present invention, an aligned (i.e. AMF/ANF/AG/ANO) coating on the luminal surface aligns both the blood flow and the growth of natural endothelial cell layers in a uniform, optimal direction (i.e. longitudinally along the central axis of the lumen). An aligned inner coating accelerates and optimizes blood flow for better drainage and support. Normal blood flow around the implant flushes out immune response agents and toxins, as they are produced, to accelerate drainage and healing. Normal blood flow also feeds the developing, natural endothelial cell layer above the artificial functional endothelial implant coating with nutrients.

Once the natural endothelial cell layer has developed to a sufficient extent (i.e. a depth of approximately 0.1 mm) and moderate amounts of beneficial (i.e. aligned) restenosis have been permitted to occur, the result is a camouflaged implant buried within normal, healthy tissue. No foreign materials are detectable by the blood and so the blood related immune response and inflammation are inhibited, thereby greatly reducing the risk of thrombosis. As therapeutic agents begin to be eluted from DES upon degradation of the aligned coating, the beneficial, controlled restenosis process ("encapsulation") comes to a halt. The implant remains stably buried but the thickness of the luminal walls stops increasing to avoid reclosure. The therapeutic agents are powerful enough to prevent additional encapsulation but cannot undo the beneficial, implant-sealing, encapsulation that has already occurred.

Elution of the therapeutic ECM suppressing therapeutic agent will arrest the proliferation of neointima (protein deposition) (see FIG. 4). Due to the delay in the onset of therapeutic agent release, by the time the therapeutic agents are released all the implant implants are encapsulated with endothelium and/or smooth muscle. Therefore, higher dosages of therapeutic agents, faster elution rates, and/or more aggressive therapeutic agents can be used to ensure maximum effectiveness in preventing restenosis and inhibiting excessive ECM thickening in the long term without fear of LST from an immune reaction. Once the implant implants are smoothly buried beneath a thin natural tissue layer thrombosis is unlikely.

Optionally, the implant may have semi-permeable cross-sectional side walls extending through the surface area of the cross section on each end adjacent to a target site to be treated with an eluted therapeutic agent. The side walls would serve as barriers to the therapeutic agent to concentrate it at the target site and avoid the negative effects of systematic therapeutic agent distribution. Such sidewalls would also conserve the therapeutic agent to be maintained where it is needed most to allow less total therapeutic agent within the implant to be equally effective by reducing the washout effect. Reducing the total therapeutic agent stored in the state (while maintaining effectiveness) is beneficial because then the implant walls can be thinner and it is also less expensive. The semi-permeable nature of the side walls allows them to permit the influx of important nutrients needed at the constricted vessel site and to permit the outflux of waste thus preserving hemodynamics. The cross-sectional side walls would dissolve naturally in time to correspond with the termination of the desired therapeutic agent treatment period.

Optionally, the implant may include radio-opaque substances in one or more of the materials of which it is formed or in one or more coatings. An array of different, distinguishable radio-opaque substances may also be used in each layer or coating. These substances would enable a physician to externally observe the placement, progress, and improvement of the implanting procedure without causing the patient discomfort from an internal inspection and without risking displacing the implant during an internal (i.e. endoscopic) inspection.

Another approach to avoiding LST while still controlling restenosis is by accelerating the endothelization of the implant through aligned scaffolding without the antirestenosis therapeutic agent. The bare implant can be made of (at least in part) or coated with elongated AMF/ANF/AG/ANO aligned with the direction of blood flow (i.e. long axis of fibers parallel to the direction of blood flow). Endothelial cells (ECs) are themselves elongated and tend to also be aligned with the direction of blood flow. By aligning the fibers with the preferred alignment of ECs, the deposition of ECs over the implant (including but not limited to the implant implants) is accelerated (aligned scaffolding). The presence of ECs tends to arrest the restenosis process (smooth muscle proliferation). The AMF/ANF/AG/ANO are preferably laid down on the inner diameter (ID) of the implant (see FIG. 3). The outer diameter (OD) or abluminal surface of the implant is typically embedded in or aligned against the luminal surface of the vessel so that the longitudinal alignment of the fibers here is not as important as for the inner diameter or luminal surface of the implant.

The implant implants are typically 50 to 100 microns wide. The fibers are preferably 0.5 to 10 microns wide. Therefore, regardless of the implant implant orientation, the fibers can have an aspect ratio of 5 or greater. By having an aspect ratio greater than 2, the fibers can provide effective longitudinally aligned scaffolding for ECs to grow on.

The AMF/ANF/AG/ANO coating or surface can be impregnated or coated with antiplatelet or anticoagulant therapeutic agents such as heparin, ticlopidine, chlopidrel, enoxaparin, dalteparin, hirudin, dextran, bivalirudin, argatroban, danparoid, Tissue Factor Pathway Inhibitor (TFPI), GPVI antagonists, antagonists to the platelet adhesion receptor (GP1b-V-IX), antagonists to the platelet aggregation receptor (GPIIb-IIIa) or any combination of the aforementioned agents.

The AMF/ANF/AG/ANO material can also be impregnated with endothelization promoting substances such as vascular endothelial growth factor (VEGF), angiopoietin-1, antibodies to CD34 receptors, and/or hirudin, dextran.

The coating can be applied to the inner diameter (ID) of the implant in the form of longitudinally aligned microfibers, nanofibers, grooves, or nitric oxide carrying elements by several modified processes of electrospinning.

1A. Aligned Nanofibers on implant implants only: A dispensing syringe is loaded with a solution of the fiber material and is charged (i.e. positive) with a high voltage (>1 kV) to charge the solution. The implant is either grounded or charged by applying the opposite voltage (i.e. negative). The outer diameter (OD) of the implant is covered with a polar or conductive tube that sticks to the fiber material well. For example, if PGA or PLA are used as the polymer solution from which the fiber material is formed, polyethylene terephthalate (PET) is heat shrunk on the OD of the implant. The implant is held by a grounded or charged (i.e. negative) collet on the OD of one end. The dispensing syringe needle with a 90 degrees bend (or side hole) at the tip is inserted inside the ID of the implant from the open end of the implant. The charged solution is dispensed from the needle tip onto the implant ID as longitudinally aligned micro/nanofibers/grooves/nitric-oxide carrying elements as the syringe tip is moved back and forth longitudinally. As the syringe tip completes one pass from one end to the other, the collet is indexed (turned incrementally) to lay down the adjacent fiber. This process continues until the whole implant ID is covered with aligned fibers, grooves or elements. Once the coating is finished, the cover (i.e. polar or conductive tube such as PET) on the OD can be peeled off to clear the implant openings of fibers.

1B. Aligned Nanofibers covering all implant: A dispensing syringe is loaded with a solution of the fiber material and is charged (i.e. positive) with a high voltage (>1 kV) to charge the solution. The implant is either grounded or charged by applying the opposite voltage (i.e. negative). The implant is held by a grounded or charged (i.e. negative) collet on the OD of one end. The dispensing syringe needle with a 90 degrees bend (or side hole) at the tip is inserted inside the ID of the implant from the open end of the implant. The charged solution is dispensed from the needle tip onto the implant ID as longitudinally aligned micro/nanofibers/grooves/nitric-oxide carrying elements as the syringe tip is moved back and forth longitudinally. As the syringe tip completes one pass from one end to the other, the collet is indexed (turned incrementally) to lay down the adjacent fiber. This process continues until the whole implant ID is covered with aligned fibers, grooves or elements.

2. The highly charged (i.e. +10 kV) syringe as described above is fixed longitudinally. The implant is grounded. A ring of opposite charge (i.e. −10 kV) is placed near the implant. The dispensing syringe is pulsed by pulsing syringe pressure, a needle valve, or charging to completely dispense one aligned fiber. The implant is then rotationally indexed for the next pulsed dispensing.

3. A hollow ring containing the solution of fiber material has series of micro/nano-holes on the end for dispensing parallel fibers arranged in a diameter close to the diameter of the implant. The ring is highly charged (i.e. +10 kV) to charge the fiber material in solution. The implant is grounded. A ring close to the diameter of the implant is charged with an opposite charge (i.e. −10 kV) on the opposite end of the implant. This charged state will cause the solution which forms the fibers to eject from the holes in parallel, longitudinally towards the oppositely charged ring while simultaneously adhering to the implant along the path from one ring to another.

In another embodiment, the inner surface of the implant implant can have micro/nano-grooves etched on it longitudinally (parallel to axis of implant). ECs will tend to grow into these grooves. The grooves are preferably 1 to 10 microns wide. In the same manner, the grooves can also be ridges or channels. The longitudinally aligned micro/nano-grooves may also be used as reservoirs or longitudinal wells for storing therapeutic agents within the aligned fiber layers for controlled or multi-phase elution.

These AMF/ANF/AG/ANO implants are particularly advantageous when applied to intravascular bifurcations or vessels with one or more corollary branch adjacent to a main lumen. Bifurcated vessels tend to have much higher rates of restenosis with both conventional BMS and DES than do non-bifurcated vessels.

The present invention controls tissue encapsulation of the implant and of injured tissue in at least three ways: biologically, geometrically, and chronologically.

Biologically, aligned nano/microfibers with or without aligned nano/microgrooves therein (or alternatively, aligned grooves formed within a non-fibrous material) facilitate functional endothelization by encouraging a uniform orientation in any cell growth that occurs (whether of true endothelial cells or artificial endothelial cells). The polymers or other materials chosen for the construction of the nano/microfibers or nano/microgrooves must be biocompatible to permit the natural flow of blood and other bodily fluids through the lumen adjacent the implant's inner surface without elicitation of an immune response or thrombosis. The materials used to form the fibers or the material within which the grooves are etched can be synthetic or naturally derived. Suitable materials include: biodegradable materials such as polyglycolic acid (PGA), polylactic acid (PLA), copolymer of PLA and PGA (PLGA), hydroxyapatite (HA), polyetherester, polyhydroxybutyrate, polyvalerate, polycaprolactone, polyanhydride, poly-ortho ester, polyiminocarbonates, polyamino acids, polyethylene glycol, polyethylene oxide, and polyvinyl alcohol; non biodegradable polymers such as fluoropolymer like Polytetrafluoroethylene (PTFE), polyzene-F, polycarbonate, carbon fiber, nylon, polyimide, Polyether ether ketone, polymethylmethacrylate, polybutylmethacrylate, polyethylene, polyolefin, silicone, and polyester; biological substances such as high density lipoprotein, collagen, fibrin, phosphorylcholine (PC), gelatin, dextran, or fibrinogen.

Geometrically, the invention is designed to only allow 0.1 mm thickness of encapsulation (of implant implants or the entire implant body and of injured tissue) before the therapeutic agent elution process begins to inhibit further encapsulation. Another aspect of geometric control is the alignment of fibers/grooves and all growth thereupon whether it be endothelial cells, smooth muscle cells, proteins, matrix fibers, or collagen fibers. Due to the structure supplied by the fibers/grooves, all subsequent in vivo growth, migration, and/or proliferation is necessarily aligned to correspond to the template set by the fibers/grooves. Aligned growth does not interfere with blood flow. Further, even if the initial natural layers of biologically derived materials deposited are not the ideal materials (i.e. smooth muscle cells instead of endothelial cells), as long as they are aligned they are suspected not to impede the deposition of the optimal materials when they come along.

Chronologically, the invention assures that the complete degradation of the polymer (or other material) layer serving as a delay coat for the antiproliferative therapeutic agent corresponds to the time when an optimal amount (i.e. 0.1 mm thickness) of encapsulation has occurred because that point in time also marks the onset of elution of the antiproliferative therapeutic agent which will suppress further thickening of tissue encapsulation. Temporal control over the elution of the antiproliferative and/or other therapeutic agents may also be achieved by an external activation means that signals for the aligned therapeutic agent reservoirs to begin elution. The external activation means may be electromagnetic radiation, infrared light, microwave radiation, x-ray radiation, etc. This type of external activation means would provide very precise control of the onset of therapeutic agent elution. Since the rate of encapsulation will vary from individual to individual and from procedure to procedure depending upon a multitude of factors, a pre-elution assessment (i.e. imaging for endothelial cell markers) of the extent of encapsulation can precede initiation of the external activation means to ensure elution does not begin prematurely.

In some embodiments, the teachings are directed to a therapeutic coating that promotes formation of a functional endothelium on a medical device. In these embodiments, the coating comprises a biodegradable drug-containing layer that is positioned over a surface of a medical device and serves as a source of a drug that functions as an antiproliferative agent in a subject. The coating also comprises a biodegradable drug-reservoir layer positioned over a surface of the drug-containing layer. The drug-reservoir layer comprises a drug-retaining layer, wherein the drug-retaining layer is void or substantially void of the drug at a time of implantation in the subject and functions to retain and at least substantially block an initial release of the drug into the subject for a time sufficient to form a functional endothelium over the surface of the medical device. In these embodiments, the functional endothelium can provide a source of thrombomodulin to the subject. It should be appreciated that the drug may be at least substantially miscible in the drug-reservoir layer to facilitate a retention of the drug. It should be appreciated that the time sufficient to form a functional endothelium may vary according to selection of subject, medical device, location of an implant, materials used, and the like. In some embodiments, the time can be at least about 20 days.

In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons. And, in some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

Moreover, the drug-retaining layer can comprise a polymer having ester-terminal groups. The polymer can have, for example, a molecular weight ranging from about 50 KDaltons to about 190 KDaltons, and a structure that remains at least substantially undegraded during the initial release of the drug, the structure comprising P—CO2R, where P is the polymer backbone and R is an alkyl group having from 1 to 4 carbons.

The coating may at least substantially promote development of the functional endothelium as the source of the thrombomodulin when compared to a control development of such endothelium formation observed following implantation of a metal or polymer drug-eluting medical device. In addition, the coating may at least substantially inhibit development of a hyperproliferative tissue when compared to a control development of such hyperproliferative tissue observed following implantation of a metal or polymer medical device that does not elute a drug. In some embodiments, the medical device comprises an implant.

The coatings can be designed for a delay time before onset of the release of the drug and elution of the drug at a certain rate. In some embodiments, the drug-reservoir layer can further comprise an accelerant layer to accelerate the onset of elution. And, in some embodiments, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons. In some embodiments, the accelerant layer can comprise a drug. The amount of drug in the accelerant layer can be 0, 5, 10, 15, 20, 25, 30, 35, 40, 45, 50, 60 percent, or any amount therein.

In fact, other variables can be used to design for a desired delay time and release rate of the drug. In some embodiments, for example, the thickness ratio of the drug-reservoir layer to the drug-containing layer can range from about 4:1 to about 10:1, and the miscibility of the drug in a coating can be preselected to affect the rate of drug migration. In some embodiments, the thickness of the coating can range from about 2 microns to about 9 microns. And, in some embodiments, the thickness ratio of the drug-retaining layer to the drug-containing layer ranges from about 4:1 to about 7:1.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. In some embodiments, the drug-reservoir layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-reservoir layer, is more hydrophilic than the remainder of the drug-reservoir layer, and comprises at least one sub-layer having a thickness of less than or equal to 3 microns, where a repeated application the sub-layer is used to form thicknesses of greater than 3 microns. The application of the sub-layers can be used to at least substantially promote a retention of the drug in the drug-containing layer during formation of the coating when compared to such a coating without the application of the sub-layers.

The coatings taught herein can, in some embodiments, further comprise pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, estradiol, and transcription factor E2F1.

In some embodiments, the teachings are directed to a medical device having a drug-retaining coating that at least substantially delays the initial elution of a drug for a time effective at forming a functional endothelium over a surface of the medical device. In some embodiments, the coatings are a switch for "turning on" drug elution at a desired time, where the switch can be programmed through coating design to elute at the desired time using the methods taught herein. In some embodiments, the coating can be designed to elute at a desired rate after the onset of elution.

Merely forming an endothelium is not the same as forming a functional endothelium. The term "functional endothelium" includes, for example, an endothelium that functions to at least provide a localized source of thrombomodulin, nitric oxide, or a combination thereof. On a functional endothelium, for example, there is typically an abundance of thrombomodulin, a protein that inhibits blood clot formation. Besides the benefits of thrombomodulin in reducing blood clots, there are several other benefits of a functional endothelium. A functional endothelium, for example, can also inhibit hyperproliferative tissue growth long term or produce nitric oxide that can allow the blood vessels to dilate to accommodate increased blood flow from exercise for example.

In some embodiments, a coating "at least substantially delays the initial elution" includes, for example, where there is no measurable elution of drug for an initial period of time, or the elution of drug over the initial period of time is negligible or sufficiently retained, such that the desired effect that would be obtained in the absence of any drug elution is still obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. And, "a time effective at forming a functional endothelium over a surface of the medical device" can be, for example, any duration of time in which the elution of drug can be entirely or partially inhibited to allow for formation of an endothelium that provides a localized source of thrombomodulin where desired, in an area of an implant. In some embodiments, the terms "block", "delay", and "retain" can be used interchangeably.

The coating can comprise a drug-containing layer applied over a surface of the medical device. In some embodiments, the drug-containing layer can be 100% drug. In some embodiments, the drug-containing layer can comprise 5, 10, 15, 20, 25, 30, 35, 40, 45, 50, 55, 60, 65, 70, 75, 80, 85, 90, 95, 99, 100 percent drug, or any amount therein.

The surface of the medical device can include any surface of a medical device, such as an implanted medical device. The surface may be, for example, a breast or buttock implant, in some embodiments. The drug-containing layer can be used to provide a drug that functions as an anti-proliferative agent; and, a drug-reservoir layer can be applied over the drug-containing coating.

In some embodiments, the drug reservoir layer can comprise a drug-retaining layer that is void or substantially void of the drug at a time of implantation in a subject. A layer can be considered "substantially void" of the drug where the layer has an almost immeasurable amount of drug in the layer, or the amount is so small that the effect on the delay in onset of drug elution is still controllable using the coatings and methods taught herein. In some embodiments, a layer is substantially void of the drug, where the amount of drug is negligible or sufficiently small, such that the desired effect of the delay in the onset of elution would be obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. In some embodiments, a layer is substantially void of drug where the drug composes less than 2.0, 1.0, 0.8, 0.6, 0.5, 0.4, 0.3, 0.2, 0.1, 0.09, 0.08, 0.07, 0.05, 0.03, 0.01, 0.001 percent of the layer, or any amount therein.

And, in some embodiments, the coating can at least substantially promote development of a functional endothelium, the functional endothelium providing an additional source of thrombomodulin when compared to a control development of an endothelium formation observed following implantation of a metal or polymer drug-eluting medical device. Moreover, in some embodiments, the coating can at least substantially inhibit development of a hyperproliferative tissue when compared to a control development of such hyperproliferative tissue observed following implantation of a metal or polymer medical device that does not elute a drug. As such, the teachings are also directed to a method of inhibiting the formation of hyperproliferative tissue and promoting the formation of a functional endothelium after implantation of a medical device in a subject. Moreover, the teachings also provide a method of obtaining one of the devices taught herein and implanting the device in a subject.

The teachings are naturally directed to include a therapeutic coating that promotes formation of a functional endothelium on a medical device. The coating comprises a biodegradable drug-containing layer that is positioned over a surface of a medical device and serves as a source of a drug that functions as an anti-proliferative agent in a subject. The coating can also comprise a biodegradable drug-reservoir layer positioned over a surface of the drug-containing layer. The drug-reservoir layer can comprise a drug-retaining layer, wherein the drug-retaining layer can be void or substantially void of the drug at a time of implantation in the subject and function to retain and at least substantially block an initial release of the drug into the subject for a time sufficient to form a functional endothelium over the surface of the medical device. As discussed, the functional endothelium can provide a beneficial source of thrombomodulin to the subject to an area affected by a medical device.

It should be appreciated that, in the embodiments taught herein, the drug may be selected by its miscibility in a preselected polymer matrix. For example, the drug may be selected because it is at least substantially miscible in the drug-reservoir layer in order to retain the drug for a desired amount of time. Or, the drug may be miscible to a preselected degree, an amount sufficient to facilitate a desired retention time of the drug. A desired retention time is facilitated, for example, in a case where a functional endothelium has formed to a desired extent. It should be appreciated that the desired retention time is facilitated where the retention time is modulated to a desired amount, and the modulation of the time can include an increase or a decrease in the retention time through altering one or more coating variables, as described herein. One of skill should appreciate, for example, that miscibility of the drug with the polymer is a variable that can modulate an affinity of the drug for the polymer, in some embodiments, thus affecting retention time.

In some embodiments, the drug and polymer are mixed or blended in solution, and one skill will appreciate that the mixes or blends can be considered substantially miscible, for example, where they mix or blend homogeneously in the desired proportions of drug to polymer, at least for the purposes of the teachings provided herein. In contrast, the mixes or blends may be considered immiscible, at least for the purposes of the teachings provided herein, where the mix or blend of polymer and drug is not homogeneous in the mix or blend in the proportions desired. In some embodiments, a drug can be considered substantially miscible in a polymer, where a homogeneous, saturated solution comprising the drug in a solvent spreads on a layer of the polymer, such that (i) the solution of the drug in the solvent has a contact angle of greater than 90 degrees on the surface of the polymer; and (ii) the layer of the polymer was formed used the same solvent. In some embodiments, the drug is substantially miscible in the polymer where the surface tension of the drug and the surface tension of the polymer are the same or similar when compared using the same solvent. A surface tension is the same, where the difference is not statistically significant, and similar, where the surface tension does not vary by more than 1, 2, 3, 4, 5, 10, 15, 20, 25, or 30 percent, in some embodiments. It should be appreciated, however, that any method known to one of skill can be used to determine the relative degree of miscibility and affinity between the drug and the polymer.

In some embodiments, the retention time of a drug can be a time sufficient amount, or an otherwise desired amount of time, chosen based on any number of parameters recognized and known to one of skill in the art of drug elution from implanted medical devices. Such parameters can vary the desired amount of time based on, for example, type of implant, location of implant, construction of implant, selection of drug, desired effect, and the like.

It should be appreciated that the "time sufficient to form a functional endothelium" may vary according to selection of subject, medical device, location of an implant, materials used, and the like. In some embodiments, the time can be at least about 20 days. In some embodiments, a sufficient amount of time can range from about 5 days to about 120 days, from about 10 days to about 90 days, from about 12 days to about 50 days, from about 14 days to about 45 days, from about 15 days to about 90 days, from about 20 days to about 60 days from about 25 days to about 45 days, from about 20 days to about 40 days, from about 20 days to about 30 days, from about 25 days to about 35 days, or any range therein.

The polymeric compositions taught herein include any desired polymer, combination of polymers, copolymers and agents known to one of skill to be useful as a medical device, or coating, as taught herein. These polymers can be biodegradable due to their labile nature, such as the labile nature of the ester groups that are present in some polymers. In some embodiments, these compositions can be designed such that they can be broken down, absorbed, resorbed and eliminated by a mammal. As such, the compositions can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and noncovalent bonds. Covalent bonds include, but are not limited to, simple covalent bonds and coordinate bonds. Non-covalent bonds include, but are not limited to, ionic bonds, and intermolecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or biobeneficial nature of the composition, While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo, such as for the release of a drug. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

In some embodiments, the compositions may be used, for example, to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article or coating formed from the polymer.

A polymer or coating can be "biodegradable," for example, when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the teachings herein may be biodegradable and may include, but are not limited to, condensation copolymers. In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons.

Biodegradable polymers can be used, and biodegradable polymers should be selected according to their behavior and hydrolysis in vivo. In some embodiments, the number average molecular weight of the polymer fragments should be at or below about 40,000 Daltons, or any range therein. In some embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of polymers that can be used in some embodiments include, but are not limited to, poly(acrylates) such as poly(butyl methacrylate), poly(ethyl methacrylate), poly (hydroxylethyl methacrylate), poly(ethyl methacrylate-co-butyl methacrylate), copolymers of ethylene-methyl methacrylate; poly(2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly (N-vinyl pyrrolidone); poly(aminocarbonates); poly(iminocarbonates); poly(anhydride-co-imides), poly(hydroxyvalerate); poly(L-lactic acid); poly(L-lactide); poly (caprolactones); poly(lactide-co-glycolide); poly (hydroxybutyrates); poly(hydroxybutyrate-co-valerate); poly(dioxanones); poly(orthoesters); poly(anhydrides); poly (glycolic acid); poly(glycolide); poly(D,L-lactic acid); poly (D,L-lactide); poly(glycolic acid-co-trimethylene carbonate); poly(phosphoesters); poly(phosphoester urethane); poly(trimethylene carbonate); poly(iminocarbonate); poly (ethylene); poly(propylene) co-poly(ether-esters) such as, for example, poly(dioxanone) and poly(ethylene oxide)/poly (lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly (ethylene-co-vinyl alcohol) (EVAL), copolymers of acrylonitrile-styrene, ABS resins, and copolymers of ethylene-vinyl acetate; poly(amides) such as Nylon 66 and poly (caprolactam); alkyd resins; poly(carbonates); poly (oxymethylenes); poly(imides); poly(ester amides); poly (ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, other polymers may be selected such that they specifically exclude any one or any combination of these polymers.

In some embodiments, the coatings can comprise one or more biodegradable polymers. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, poly(ester amides); amino acids; PEG and/or alcohol groups, polycaprolactones, poly(L-lactide), poly(D,L-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof. In some embodiments, the polymers can include poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of these polymers.

In some embodiments, the polymers can be chemically connected by covalent bonds. In some embodiments, the polymers can be chemically connected to by non-covalent bonds such as, for example, by ionic bonds, inter-molecular attractions, or a combination thereof. In some embodiments, the polymers can be physically connected. In some embodiments, the polymers can be chemically and physically connected. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed.

The behavior of the polymer matrix can be changed through selection of any number of factors that provide the desired drug elution, chemical and physical characteristics of the coatings taught herein. For example, the terminal end groups can be designed to contribute to imparting such characteristics in the polymers. A more hydrophilic end-group can increase the rate of ingress of water, for example, and likewise increase the rate of hydrolysis of the polymer chains, at least in some embodiments. Likewise, a less hydrophilic group can deter in the ingress of water, and slow the rate of hydrolysis, at least in some embodiments.

It should be appreciated that a polymer can be selected to have acid terminal end-groups, hydroxyl terminal end-groups, alkyl-ester end-groups, or a combination thereof. Moreover, a polymer layer can be created using sub-layers, where the layer can have a sub-layer having acid groups, a sub-layer having hydroxyl groups, a sub-layer having ester end-groups, or a combination thereof. In fact, the construction of the layers and sub-layers can be designed based on thickness ratios to design a coating that provides a desired characteristic or set of characteristics including, but not limited to, drug-retention time, a desired rate of hydrolysis, a desired glass transition temperature, a desired drug-elution rate, a desired toughness, a desired elasticity, a desired modulus, or a combination thereof.

Molecular weights can also be selected for the polymer in a particular layer or set of layers in the coating, as a mixture of molecular weights in a particular layer or set of layers, or as a set of sub-layers, where each layer in the sub-layer can have an independently selected molecular weight, mixture of molecular weights, or a combination thereof, where the molecular weight or mixture of molecular weights can be the same or different for each sub-layer. And, in many embodiments, a desired characteristic is that the polymers have a structure that remains at least substantially undegraded during the initial release of the drug. In some embodiments, for example, the drug-retaining layer can comprise a polymer having ester-terminal groups.

In some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

The molecular weights can be selected and tailored for a particular polymer selection and for a particular coating layer and purpose. For example, the polymer can have a molecular weight ranging from about 50 KDaltons to about 190 KDaltons, from about 50 KDaltons to about 190 KDaltons, from about 50 KDaltons to about 180 KDaltons, from about 60 KDaltons to about 170 KDaltons, from about 70 KDaltons to about 160 KDaltons, from about 80 KDaltons to about 150 KDaltons, from about 90 KDaltons to about 140 KDaltons, from about 90 KDaltons to about 160 KDaltons, from about 100 KDaltons to about 160 KDaltons, or any range therein.

Without intending to be bound by any theory or mechanism of action, in some embodiments, the drug-reservoir layer is initially implanted in a "drug-absorbing" state and is later transformed into a "drug-release" state over time due to changes in the physical and chemical structure across the coating in vivo. In the drug-absorbing state, the drug-reservoir layer has the highest affinity for the drug. In the drug-release state the drug-reservoir layer has a substantially lower affinity for the drug. The drug can have the highest solubility in the drug-reservoir layer in the drug-absorbing state and in the drug-release state, the drug can have a substantially lower solubility in the drug-reservoir layer. In some embodiments, the drug-absorbing state can reflect the state in which the glass transition temperature (Tg) of the drug-reservoir layer is higher than the temperature of the surrounding tissue/fluid, and the drug-release state can reflect the state at which the Tg of drug-reservoir layer is equal to or less than that of surrounding tissue/fluid. In some embodiments, coating has a Tg above the surrounding tissue temperature of 37 degrees C.

The polymer end-groups can have any structure known to one of skill that will provide the desired polymer characteristics for a particular coating layer or set of layers. In some embodiments, the end-group can be an ester-terminal group. For example, the polymer structure can comprise P—CO2R, where P is the polymer backbone and R can be an alkyl group having from 1 to 4 carbons, from 1 to 20 carbons, from 2 to 12 carbons, from 1 to 10, from 2 to 8, from 1 to 6 carbons, from 1 to 5 carbons, or any range therein. In some embodiments, R can be any end-group known to one of skill, with the limitation that R cannot affect usefulness of the polymer, for example, the ability of the polymer to be applied as a coating on a desired medical device. In some embodiments, R can be saturated, unsaturated, aromatic, aliphatic, or any combination thereof.

In some embodiments, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, isobutyl, t-butyl or iso-hexyl; upper alkyl groups such as for example, n-heptyl, n-octyl, isooctyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, non-ene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six $\pi$ (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms. In some embodiments, a radical is straight-chained if it has less than 0.01 mole percent of such side chains. In some embodiments, a radical is straight-chained if it has less than 0.001 mole percent of such side chains. A radical is "branched" when it has more than 0.1 mole percent of side chains having 1 or more carbon atoms. In some embodiments, a radical is branched when it has more than 0.01 mole percent of such side chains. In some embodiments, a radical is branched when it has more than 0.001 mole percent of such side chains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In some embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In some embodiments, the functional groups are capable of free-radical polymerization and can include, but are not limited to, ethylenically unsaturated groups such as, for example, allyl, vinyl, acryloyl and methacryloyl, and maleate and maleimido; and combinations thereof. In some embodiments, the functional groups include halides. In some embodiments, the functional group may include light scattering groups, magnetic groups, nanogold, other proteins, a solid matrix, radiolabels, carbohydrates, and combinations thereof.

The coating may at least substantially promote development of the functional endothelium as the source of the thrombomodulin when compared to a control development of such endothelium formation observed following implantation of a metal or polymer drug-eluting medical device. In some embodiments, the medical device comprises an implant.

One of skill will appreciate that a functional endothelium exists, or is promoted, for example, where the amount of thrombomodulin in the functional endothelium is in a quantity sufficient to show a statistical difference in an amount of thrombus formation when compared to a control development of such an endothelium, or lack thereof, observed following implantation of a control metal or polymer drug-eluting device. In some embodiments, the functional endothelium has been promoted where it can produce an amount of thrombomodulin that is substantially greater than an amount of thrombomodulin observed from a control medical device. An amount of thrombomodulin is "substantially greater" when the desired anti-thrombus effect is statistically improved over that observed from a control medical device. In some embodiments, a functional endothelium exists, or has been promoted, where the desired effects of thrombus inhibition, restenosis inhibition, and/or blood flow improvement from the presence of thrombomodulin becomes statistically observable when compared to a control development of such endothelium formation observed following implantation of a metal or polymer drug-eluting medical device that does not delay the onset of drug-elution for at least 5, 10, 12, 14, 15, 20, 25, 30, 45, 60, 75, or 90 days, or any range therein.

In addition, the coating may at least substantially inhibit development of a hyperproliferative tissue when compared to a control development of such hyperproliferative tissue observed following implantation of a metal or polymer medical device that does not elute a drug. One of skill will appreciate, for example, that hyperproliferative tissue growth includes a growth of tissue beyond what is normal and healthy. It can cause adverse effects on the function or physiology of the subject.

The inhibition of the development of a hyperproliferative tissue can occur, or be promoted, when the amount of such tissue is in a quantity sufficient to show a statistical difference in an amount of tissue formation when compared to a control development of such an tissue, or lack thereof, observed following implantation of a control metal or polymer medical device that does not elute a drug. In some embodiments, the amount of hyperproliferative tissue produced from the control device is substantially greater than an amount of tissue observed from a medical device having a coating taught herein. An amount of tissue can be considered "substantially greater" when the measured amount is statistically greater. In some embodiments, restenosis is inhibited by at least 5, 10, 12, 14, 15, 20, 25, 30, 45, 60, 75, 90, 95, 99, 100 percent, or any amount therein, when compared to a control development of such restenosis formation observed following implantation of a metal or polymer medical device that does not elute a drug.

The coatings can be designed for a predetermined delay time and release rate of the drug. As described above, layers and sub-layers of coatings can be designed to have a different composition to impart more control over drug elution, coating hydrolysis, coating strength and integrity, other physical traits, and other such coating characteristics known to one of skill. In some embodiments, for example, the drug-reservoir layer can further comprise an accelerant layer to accelerate the time to onset of drug elution. In fact, in some embodiments, the accelerant layer can have a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons.

And, as described above, other variables, such as layer or sub-layer thickness, and/or thickness ratios between layers and/or sub-layers, can be used to obtain a desired delay time for drug release, release rate of the drug, fluid uptake in the coating, as well as coating strength, integrity, and the like. In some embodiments, the thickness of the coating can range from about 2 microns to about 9 microns, from about 1 micron to about 40 microns, from about 1 micron to about 30 microns, from about 2 microns to about 38 microns, from about 3 microns to about 36 microns, from about 4 microns to about 34 microns, from about 5 microns to about 7 microns, from about 4 microns to about 6 microns, or any range therein. In some embodiments, the thickness of the coating is less than 12 microns, less than 11 microns, less than 9 microns, less than 8 microns, less than 7 microns, less than 6 microns, less than 5 microns, or any range therein, such as, for example, from 7 microns to 12 microns, 9 microns to 12 microns, or 7 microns to 9 microns. In some embodiments, each layer or sub-layer can range from about 0.1 micron to about 10 microns, from about 0.1 micron to about 7 microns, from about 0.1 micron to about 5 microns, from about 0.1 micron to 3 microns, from about 0.1 micron to about 2 microns, from about 0.1 micron to about 0.9 microns, from about 0.1 micron to about 0.8 microns, from about 0.1 micron to about 0.7 microns, from about 0.1 micron to about 0.6 microns, from about 0.1 micron to about 0.5 microns, from about 0.1 micron to about 0.4 microns, from about 0.1 micron to about 0.3 microns, from about 0.3 micron to about 0.8 microns, from about 0.2 microns to about 5 microns, from about 0.2 microns to about 4 microns, from about 0.3 microns to about 3 microns, from about 0.5 microns to about 5 microns, from about 0.6 microns to about 3 microns from about 1 micron to about 3 microns, or any range therein.

In some embodiments, for example, the thickness ratio of the drug-reservoir layer to the drug-containing layer can range from about 4:1 to about 10:1, from about 4:1 to about 7:1, from about 2:1 to about 12:1, from about 3:1 to about 11:1, from about 5:1 to about 10:1, from about 2:1 to about 8:1, from about 4:1 to about 6:1, or any range therein. In some embodiments, the ratio can be a mass ratio, where the mass of the drug-reservoir layer to the mass of the drug-containing layer can range from 3:1 to 20:1, from 4:1 to 16:1, from 5:1 to 15:1, from 6:1 to 10:1, or any range therein.

In some embodiments thinner coatings and desired ratios can be achieved using higher percentages of drug in the drug-containing layer, where in some embodiments, the drug-containing layer is composed of 100, 99, 98, 97, 96, 95, 94, 93, 92, 91, 90 percent drug, or any range therein. The drug-containing layer can range from about 0.05 to about 5 microns, from about 0.03 to about 3 microns, from about 0.1 to about 2 microns, or any range therein in thickness, in some embodiments.

The relative hydrophobicity or hydrophilicity can also impart desired drug retention and elution behavior from the coating. For example, the miscibility of the drug in a coating can be preselected to affect the rate of drug migration in the coating, and/or elution from the coating. In some embodiments, the drug can be selected to be miscible in a coating to increase retention time in the coating. Likewise, in some embodiments, the drug can be selected to be less miscible, or immiscible, in a coating to decrease retention time in the coating.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

One of skill will appreciate that a coating can be applied using any one, or any combination, of methods known in the art, where the terms "form" and "apply" can be used interchangeably, in some embodiments. The compositions can be in the form of coatings for medical devices such as, for example, a balloon-expandable breast implant. There are many coating configurations possible, and each configuration can include any number and combination of layers. In some embodiments, the coatings can comprise one or a combination of the following four types of layers: (a) an agent layer, which may comprise a polymer and an agent or, alternatively, a polymer free agent; (b) an optional primer layer, which may improve adhesion of subsequent layers on the implantable substrate or on a previously formed layer; (c) an optional topcoat layer, which may serve as a way of controlling the rate of release of an agent; and (d) an optional biocompatible finishing layer, which may improve the biocompatibility of the coating.

In some embodiments, any one or any combination of layers can be used. And, each layer can be applied to an implantable substrate, for example, by any method including, but not limited to, dipping, spraying, pouring, brushing, spin-coating, roller coating, meniscus coating, powder coating, inkjet-type application or a combination thereof. In one example, each of the layers can be formed on an implant by dissolving one or more biodegradable polymers, optionally with a non-biodegradable polymer, in one or more solvents and either (i) spraying the solution on the implant or (ii) dipping the implant in the solution. In this example, a dry coating of biodegradable polymer may be formed on the implant when the solvent evaporates.

The formation of each layer may involve use of a casting solvent. A casting solvent is a liquid medium within which a polymer can be solubilized to form a solution that may be applied as a coating on a substrate. The casting solvent must be selected to avoid adversely affecting an underlying material such as, for example, an underlying primer layer or a bare implant structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, ability to hydrogen bond, molecular size, volatility, biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, InC) (10:40:50 w/w); and 1,1,2-trichloroethane and chloroform (80:20 w/w).

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures.

A medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30 degrees C. to about 200 degrees C., from about 35 degrees C. to about 190 degrees C., from about 40 degrees C. to about 180 degrees C., from about 45 degrees C. to about 175 degrees C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. The amount of mobilization of the drug can be considered "substantially inhibited" when the measured amount of mobilization of the drug from the drug-containing layer is statistically less than if the drying procedure was not used as taught herein.

The application of the sub-layers can be used to at least substantially promote a retention of the drug in the drug-containing layer during formation of the coating when compared to such a coating without the application of the sub-layers. The amount of retention of the drug can be considered "substantially promoted" when the measured amount of retention of the drug from the drug-containing layer is statistically greater than if the sub-layer application as taught herein was not used.

In some embodiments, the drug-retaining layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-retaining layer, is more hydrophilic than the remainder of the drug-retaining layer, and comprises at least one sub-layer having a thickness of less than or equal to 3 microns, where a repeated application the sub-layer is used to form thicknesses of greater than 3 microns. The accelerant layer can contain some of the drug. In some embodiments, the drug composes less than 30, 25, 20, 15, 10, 7, 5, 4, 3, 2, 1 percent, or any amount therein, of the accelerant layer. And, in some embodiments the drug composes less than 10 percent of the accelerant layer.

The coatings can be heterogeneous in morphology. For example, a hydrophobic layer can contain hydrophilic regions. Likewise, a more hydrophilic coating can have hydrophobic regions. The hydrophilic regions can be in the form of isolated packages of material, or "islands" in some embodiments, where the isolated hydrophilic package can add to the water absorption rate, and thus hydrolysis rate, of the coating. The isolated packages may be added during the coating process as droplets, in some embodiments. The coatings taught herein can, in some embodiments, further comprise pockets of hydrophilic material in the drug-retaining layer, wherein the hydrophilic material can comprise a second drug. There can be one or more such pockets, and the pockets can be positioned anywhere throughout the coating. In some embodiments, one or more hydrophilic pockets are positioned in the drug reservoir layer and, in some embodiments, one or more hydrophilic pockets are positioned in the drug-retaining layer. In some embodiments, the hydrophilic pockets comprise a drug selected from the group consisting of dextran, heparin, ticlopidine, chlopidogrel, enoxaparin, dalteparin, hirudin, bivalirudin, argatroban, and danparoid.

The coating can be applied to a surface of a medical device using, for example, wet chemistry and acetone as a solvent with techniques known to one of skill. At least one drug and polymer is dissolved into the volatile solvent to form a drug solution, and the drug can be an anti-proliferative, such as rapamycin. The volatile solvent can be acetone, dichloromethane, or a mixture of the two solvents.

In one example, about 1-2 micron of a drug-containing layer can be covered with a 1-3 micron accelerant layer made of acid terminated 75/25 monomer ratio PLGA having a molecular weight of 90-120 KDalton, and the accelerant layer can be covered with about 6-12 microns of ester terminated 75/25 monomer ratio PLGA having a molecular weight of 100-160 KDalton. This unique and novel combination of compositions in different layers, as well as the relative thicknesses and positioning of the layers, can provide a coating having a desired delay in the onset of drug elution. The elution, in fact, can be delayed for a designed, prolonged period of time, at which time the drug release is fast enough to have a therapeutic effect. The coating is robust, maintaining functional integrity through stresses and strains of assembly and deployment. And, the coating can maintain a low enough profile of the implant for ease of delivery and introducing less foreign material into the body.

The following is an example of a process that can be used to create composite elution layers, a process comprising multiple sub-layer applications, such as those described herein. The drug is added to the solvent for wet chemistry application, and the drug-containing layer may be applied to the surface of the device. The drug-containing layer can be 120 nanometers and 6 microns, 200 nanometers and 3 microns, 0.7-1.1 microns, or any range therein, thick in some embodiments. The drug-containing layer is then dried with convection of a non reactive gas, such as nitrogen, at a temperature elevated above room temperature.

The accelerant layer polymer is mixed with a solvent for wet chemistry application, and the accelerant layer is created by layering multiple sub-layers of the same material. Each sub-layer is coated onto previous layer and dried with convection of gas as described in above using a drying time of about 1-2 hours before coating the next sub-layer/layer. The accelerant layer can be about 1-2 microns thick and composed of 50:50 PLGA with acid terminal end-groups. In some embodiments, the accelerant layer can be about 3-5 microns thick and composed of 2-3 sub-layers of 75:25 PLGA with acid terminal end-groups. And, in some embodiments, the accelerant layer can be between about 120 nanometers and 6 microns, 400 nanometers and 4 microns, 500 nanometers and 5 microns, or any range therein. Moreover, the concentration of the drug in the accelerant layer can be less than 50% of the drug-containing layer before implantation in some embodiments.

The drug-retaining layer can then be prepared and coated onto the accelerant layer and dried. The drug-retaining layer is applied by layering multiple sub-layers of the same material. Each sub-layer is coated onto previous layer and dried using convection of gas as described above with drying times of about 1-2 hours before coating the next sub-layer/layer. The drug-retaining layer can be about 3-5 times the thickness of the accelerant layer, in some embodiments, if the accelerant layer is composed of 50:50 PLGA having an ester terminal end-group in some embodiments. In some embodiments, the thickness of the drug-retaining layer can be about 0.2-2 times that of the accelerant layer, if the accelerant layer is composed of 75:25 PLGA having an ester terminal end-group. The entire assembly may then be packaged and sterilized for deployment.

One of skill will appreciate that any non-reactive or substantially non-reactive gas can be used including, but not limited to, nitrogen, carbon dioxide, or a noble gas. The heated gas's temperature can be, for example, between about 70 degrees F. and the drug's melting point. In some embodiments, the gas's temperature can be between about 70 degrees F. and 240 degrees F., from 140-190 degrees F., or any range therein. The specified drying time can be, for example, between about 0 minutes and 3 hours, 10-30 minutes, 30 minutes and 1 hour, 15 minutes and 2 hours, or any range therein. The gas surface flow rate can be between about 40 and 500 inches per second, 50 and 400 inches per second, 100 and 500 inches per second, or any range therein. In some embodiments, the gas surface flow rate is 90-150 inches/seC It should be appreciated that, in some embodiments, the term "agent" or "drug" can be used interchangeably. An "agent" or "drug" can be a moiety, for example, that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope the invention.

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly(acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the teachings herein include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin Il actinomycin Xl, actinomycin Cl, and dactinomycin (COSMEGEN, Merck & Co., InC). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, InC) and mitomycin (MUTAMYCIN, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethyl ketone (synthetic antithrombin), dipyridamole, glycoprotein IIb/IIIa platelet membrane receptor antagonist antibody, recombinant hirudin, and thrombin inhibitors (ANGIOMAX, Biogen, InC), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINIVIL and PRINZIDE, Merck & Co., InC); calcium channel blockers such as nifedipine; colchicines; fibroblast growth factor (FGF) antagonists, fish oil (omega 3-fatty acid); histamine antagonists; lovastatin (MEVACOR, Merck & Co., InC); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST, Santen, InC), and any prodrugs, metabolites, analogs, homologues, congeners, derivatives, salts and combinations thereof.

Other bioactive agents useful in the teachings herein include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidine-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof. The drugs eluted from the coatings taught herein can function as an anti-proliferative or immunosuppressant. In some embodiments, the drug can be rapamycin or a derivative of rapamycin. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, and estradiol. One of skill will appreciate that agents that affect vascular smooth muscle cell (VSMC) proliferation or migration can also be used in some embodiments, including, but not limited to transcription factor E2F1.

The agents of the present invention can be used alone or in combination with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject in a desired amount to obtain a desired effect. In some embodiments, the desired amount is termed an "effective amount," where the amount administered elicits a desired response. In some embodiments, the effective amount can be a "therapeutically effective amount", administered in an amount that prevents, inhibits, or ameliorates the symptoms of a disease.

It is to be appreciated that the design of a composition for drug release can be dependent on a variety of factors such as, for example, the therapeutic, prophylactic, ameliorative or diagnostic needs of a patient or condition. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The medical devices discussed herein can be any devices known to one of skill to benefit from the teachings provided. A medical device, for example, can be comprised of a metal or an alloy, including, but not limited to, ELASTINITE, NITINOL, stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (EL-GILOY, Elgiloy Specialty Metals, InC; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that, are comprised of bioabsorbable polymers or biostable polymers are also included within the scope of the present invention.

The terms "plasticizer" and "plasticizing agent" can be used interchangeably in the teachings herein, and refer to any agent, including any agent described above, where the agent can be added to a polymeric composition to modify the mechanical properties of the composition or a product formed from the composition. Plasticizers can be added, for example, to reduce crystallinity, lower the glass-transition temperature (Tg), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarin oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight.

The amount of plasticizer used in the teachings herein, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the teachings herein. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

One embodiment applies gamma irradiation or electron beam (e-beam) sterilization. Other types of radiosterilization can be used.

In some embodiments, the drug-containing layer may be applied to a surface of a prosthesis, and the drug-reservoir layer may be applied on or over the drug layer. In some embodiments, the prosthesis can comprise a fitting for mechanically coupling to an adjacent tissue, such as calcified or soft tissue, for example, a bone implant or intra-organ implant. In some embodiments, the system may comprise an entirely resorbable construct, such as a capsule, a tablet, a pellet, a shaft, a rod, a sphere, disc, or a ring. In some embodiments, the resorbable construct may be configured for deployment in an anatomic environment such as the gastrointestinal tract, a synovial joint, a cardiovascular lumen, a cardiovascular chamber, a urinary lumen, a urinary chamber, a reproductive lumen, a reproductive chamber, a gynecological lumen, a gynecological chamber, an endocrine lumen, or an endocrine chamber.

In one example, a tubular drain system can be implanted, leading from one of the ventricles of the brain to an abdominal position. One or more portions, or all, or the drain system may be coated and configured to promote endothelization/healing by substantially blocking elution of antiproliferative drugs, before controllably eluting drugs to prevent excessive fibrous cellular encapsulation and/or stenosis.

In another example, portions of a "venous" needle or "arterial" needle in an arteriovenous fistula may be coated and configured to promote endothelization/healing by substantially blocking elution of antiproliferative drugs, before controllably eluting drugs to prevent stenosis and/or excessive cellular encapsulation. Many transcutaneous port or cannulation device configurations may be so treated.

In another example, portions of pacemaker, defibrillator, or other implantable device leads, such as a distal portion configured to engage a portion of the endocardial wall, may be coated and configured to promote endothelization/healing by substantially blocking elution of antiproliferative drugs, before controllably eluting drugs to prevent excessive cellular encapsulation.

In another example, portions of an intraocular lens prosthesis, such as the main body or legs of the prosthesis may be coated and configured to promote endothelization/healing by substantially blocking elution of antiproliferative drugs, before controllably eluting drugs to prevent excessive cellular encapsulation.

In another example, portions of a bile duct or other duct, tube, vessel, or lumen prosthesis may be coated and configured to promote endothelization/healing by substantially blocking elution of antiproliferative drugs, before controllably eluting drugs to prevent stenosis and/or excessive cellular encapsulation.

In another example, pellets or small prostheses used to treat tissue volumes such as those of a prostate gland may be coated and configured to promote endothelization/healing by substantially blocking elution of antiproliferative drugs, before controllably eluting drugs.

In another example, immunosuppressants and/or cytotoxics, such as taxol, can be delivered in such devices to aid in the treatment of tumors, such as prostate or other tumors. Pellets containing such drugs, for example, may be delivered through the urethra or by other surgical means.

In another example, severed nerve portions may be joined with a graft comprising an outer sheath of coated drug eluting material configured to protect and isolate the inner graft material while also promoting endothelization/healing by substantially blocking elution of antiproliferative drugs, before controllably eluting drugs to discourage excessive cellular overgrowth which may lead to nerve impingement and/or adhesion.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims. In accordance with another aspect, the fastener portion is formed monolithic with the head portion, as controlled by a computer so that the fastener/head portion conforms to the patient's body for better fit.

An embodiment of the invention can be used where two or more segments of bone need to be aligned and require flexibility and changes of material properties based on temperature when device is placed.

An embodiment of the invention can help with broken bones, trauma, or other types of surgery but also building design or transportation design.

All references, patents, patent applications or other documents cited are hereby incorporated by reference herein in their entirety.

A natural feel is achieved through viscoelastic harmony of properties between the existing tissue and the implant. This can be done by manipulating the viscous component of the implant through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in dermal filling applications. Other advantages and features include: longevity without touch up, hyper-volumic degradation, anatomic compliant and iso-osmotic controlled, among others.

The present invention has been described particularly in connection with a breast, butt, or body implant, among others, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof. Variations and modifications can, of course, be made without departing from the spirit and scope of the invention.

What is claimed is:

1. A method, comprising:
   forming a scaffold and seeding the scaffold with live cells;
   growing the cells in the scaffold;
   determining a boundary of the skin wound through a hand-held dispenser with a camera to capture an image of the selected area and a processor to perform image processing and actuate a dispensing head; and
   3D printing the cells over the determined boundary of the selected area with the hand-held dispenser.

2. The method of claim 1, comprising printing a three-dimensional-shaped scaffold.

3. The method of claim 1, wherein the forming the scaffold further comprises:
   depositing deionized water in a vessel;
   adding carbomer, allantoin, dipotassium glycerrhizate, and disodium ethylenediaminetetraacetic acid into a batch and mixing the batch for a predetermined period;
   adding collagen and mixing the batch;
   adding triethanolamine and mixing the batch; and
   phosphorylating the collagen with Phosphorus or Orthophosphoric Acid.

4. The method of claim 1, wherein the forming the scaffold further comprises mixing Propylene Glycol, *Spiraea ulmaria* Flower Extract, *Centella asiatica* Extract, and one or more Amino Acids.

5. The method of claim 1, wherein the forming the scaffold further comprises mixing Algae Extract, Mugwort Extract, or *Artemisia Vulgaris* Extract.

6. The method of claim 1, wherein the forming the scaffold further comprises mixing Phenoxyethanol-Methylparaben-Ethylparaben-n-Propylparaben-n-Butylparaben-iso-Butylparaben.

7. The method of claim 1, wherein the forming the scaffold further comprises mixing Sodium Ascorbyl Phosphate or Vitamin C.

8. The method of claim 1, wherein the forming the scaffold further comprises mixing Aloe Barbadensis Leaf Extract.

9. The method of claim 1, wherein the forming the scaffold further comprises Butylene Glycol, Panthenol, *Crithmum maritimum* extract.

10. The method of claim 1, comprising determining a dispensing target using computer vision and selectively dispensing cells as guided by a camera.

11. A method, comprising:
preparing a live cell suspension;
imaging a target region using a camera;
determining a boundary of the skin wound through a hand-held dispenser with a camera to capture an image of the target region and a processor to perform image processing and actuate a dispensing head on the hand-held dispenser; and
printing over the determined skin boundary a solution to form an acellular dermal matrix (ADM) scaffold with the live cell suspension.

12. The method of claim 11, comprising 3d printing an arbitrarily shaped scaffold.

13. The method of claim 11, comprising printing a quantity of harvested skin cells.

14. The method of claim 11, comprising wherein the scaffold comprises a photocrosslinkable interpenetrating polymeric network (IPN) of collagen and hyaluronic acid (HA).

15. The method of claim 11, comprising surgically implanting an object into a living subject, where the cells continue to live in the living subject.

16. The method of claim 11, comprising printing materials with nerve tissues.

17. The method of claim 11, comprising printing materials with stem cells.

18. The method of claim 11, comprising injecting one or more bio-materials using a syringe.

19. The method of claim 11, comprising transmitting a target area image to a remote medical professional.

* * * * *